US009920100B2

(12) United States Patent
Leung et al.

(10) Patent No.: US 9,920,100 B2
(45) Date of Patent: Mar. 20, 2018

(54) MIMOTOPES OF TROPOMYOSIN FOR USE IN IMMUNOTHERAPY FOR SHELLFISH AND/OR ARTHROPOD ALLERGY

(71) Applicant: THE REGENTS OF THE UNIVERSITY OF CALIFORNIA, Oakland, CA (US)

(72) Inventors: Patrick Leung, Davis, CA (US); Ka Hou Chu, Kowloon (HK); Yee Yan Wai, Kowloon (HK); Yat Hin Nicki Leung, Tai Wai (HK)

(73) Assignees: The Chinese University of Hong Kong, Hong Kong (CN); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/173,467

(22) Filed: Jun. 3, 2016

(65) Prior Publication Data

US 2016/0355555 A1     Dec. 8, 2016

(51) Int. Cl.
| | |
|---|---|
| A61P 37/08 | (2006.01) |
| C07K 7/06 | (2006.01) |
| A61K 38/08 | (2006.01) |
| C07K 14/435 | (2006.01) |
| A61K 47/48 | (2006.01) |
| A61K 39/35 | (2006.01) |
| A61K 39/00 | (2006.01) |

(52) U.S. Cl.
CPC ........ *C07K 14/43509* (2013.01); *A61K 38/08* (2013.01); *A61K 39/35* (2013.01); *A61K 47/4833* (2013.01); *A61K 47/48284* (2013.01); *C07K 7/06* (2013.01); *A61K 2039/55505* (2013.01); *A61K 2039/577* (2013.01); *A61K 2039/6081* (2013.01); *A61K 2039/70* (2013.01)

(58) Field of Classification Search
None
See application file for complete search history.

(56) References Cited

U.S. PATENT DOCUMENTS

| 4,405,712 A | 9/1983 | Vande Woude et al. |
| 2002/0077289 A1 | 6/2002 | MacDonald et al. |
| 2003/0049237 A1 | 3/2003 | Bannon et al. |

FOREIGN PATENT DOCUMENTS

| EP | 0178220 A2 | 4/1986 |
| WO | 92/06180 | 4/1992 |
| WO | 92/07943 | 5/1992 |
| WO | 93/14188 | 7/1993 |
| WO | 93/20221 | 10/1993 |
| WO | 94/06923 | 3/1994 |
| WO | 00/74716 A2 | 12/2000 |
| WO | 01/34186 A1 | 5/2001 |

OTHER PUBLICATIONS

Record for U5VT16, Jan. 22, 2014, UniProt database, 1 page as printed, no author listed.*
Lam et al, 1996. Methods: A Companion to Methods in Enzymology. 9: 482-493.*
Aina et al., From Combinatorial Chemistry to Cancer-Targeting Peptides, Molecular Pharmaceutics, 2007, vol. 4, No. 5, pp. 631-651.
Arnold et al., The Swiss-Model workspace: a web-based environemnt for protein structure homology modeling, Bioinformatics, 2006, vol. 22, No. 2, pp. 195-201.
Ayuso et al., Molecular Basis of Arthropod Cross-Reactivity: IgE-Binding Cross-Reactive Epitopes of Shrimp, House Dust Mite and Cockroach Tropomyosins, Int Arch Allergy Immunol, 2002, vol. 129, pp. 38-48.
Ayuso et al., Identification of Continuous, Allergenic Regions of the Major Shrimp Allergen Pen a 1 (Tropomyosin), Int. Arch. Allergy Immunol., 2002, vol. 127, pp. 27-37.
Chen et al., On-Bead Screening of Combinatorial Libraries: Reduction of Nonspecific Binding by Decreasing Surface Ligand Density, J. Comb Chem, 2009, vol. 11, No. 4, pp. 604-611.
Cho et al., High-Throughput Screening of One-Bead-One-Compound Peptide Libraries Using Intact Cells, ACS Comb. Sci., Jul. 2, 2013, vol. 15, pp. 393-400, doi:10.1021/cc9000168.
Chu et al., Tropomyosin Is the Major Mollusk Allergen: Reverse Transcriptase Polymerase Chain Reaction, Expression and IgE Reactivity, Mar. Biotechnol., 2000, vol. 2, pp. 499-509.
Chu et al., Multiple Strategies to Develop Allergen-Specific Immunotherapy for Shellfish Allergy, School of Life Sciences, The Chinese University of Hong Kong, May 2015, Abstract, retrieved from World Aquaculture Society on Jun. 19, 2017, 3 pages.
Ellis et al., Phage-display library biopanning as a novel approach to identifying nematode vaccine antigens, Parasite Immunology, 2012, vol. 34, pp. 285-295.
Franz et al., High-Throughput One-Bead-One-Compound Approach to Peptide-Encoded Combinatorial Libraries: MALDI-MS Analysis of Single TentaGel Beads, J. Comb. Chem., 2003, vol. 5, pp. 125-137.
Ganglberger et al., Allergen mimotopes for 3-dimensional epitope search and induction of antibodies inhibiting human IgE, The FASEB Journal, Nov. 2000, vol. 14, No. 14 , pp. 2177-2184.
Geysen et al., A Priori Delineation of a Peptide Which Mimics a Discontinuous Antigenic Determinant, Molecular Immunology, 1986, vol. 23, No. 7, pp. 709-715.
Gray et al., Combinatorial Peptide Libraries: Mining for Cell-Binding Peptides, Chem Rev., Jan. 22, 2014; vol. 114, No. 2, pp. 1020-1081; doi:10.1021/cr400166n.
Gray et el., From Phage Display to Nanoparticle Delivery: Functionalizing Liposomes with Multivalent Peptides Improves Targeting to a Cancer Biomarker, Bioconjug Chem., Jan. 16, 2013, vol. 24, No. 1, pp. 85-96; doi:10.1021/bc300498d.

(Continued)

*Primary Examiner* — Zachary Howard
(74) *Attorney, Agent, or Firm* — Kilpatrick Townsend & Stockton LLP

(57) ABSTRACT

The present invention provides isolated peptides and nucleic acids encoding the isolated peptides that can modify a subject's immune response to tropomyosin. The isolated peptides correspond to peptide epitope mimics that are based on an invertebrate tropomyosin allergen, e.g., the shrimp tropomyosin Met e 1. Also provided are compositions and methods of use thereof to reduce, minimize or eliminate an allergic response to arthropods and/or shellfish.

20 Claims, 8 Drawing Sheets

(56) References Cited

OTHER PUBLICATIONS

Hantusch et al., Mapping of conformational IgE epitopes on Phl p 5a by using mimotopes from a phage display library, J Allergy Clin Immunol., vol. 114, No. 6, pp. 1294-1300.
Huang et al., MimoDB 2.0: a mimotope database and beyond, Nucleic Acids Research, 2012, vol. 40, Database issue D271-D277; doi:10.1093/nar/gkr922.
Joyce et al., An oligosaccharide-based HIV-1 2G12 mimotope vaccine induces carbohydrate-specific antibodies that fail to neutralize HIV-1 virions, PNAS, Oct. 14, 2008, vol. 105, No. 41, pp. 15684-15689.
Knittelfelder et al., Mimotope vaccination—from allergy to cancer, Expert Opin Biol Ther, Apr. 2009, Vo. 9, No. 4, pp. 493-506; doi:10.1517/14712590902870386.
Kung, W. Y., Identification of T Cell Epitopes in the Major Shrimp Allergen, Met e 1, A Thesis Submitted in Partial Fulfilment of the Requirements for the Degree of Master of Philosophy in Biology, The Chinese University of Hong Kong, Sep. 2008, 135 pages.
Lam et al., A new type of synthetic peptide library for identifying ligand-binding activity, Nature, Nov. 7, 1991, vol. 354, pp. 82-84.
Lee et al., Rapid Microwave-Assisted CNBr Cleavage of Bead-Bound Peptides, J. Comb. Chem., 2008, vol. 10, No. 6, pp. 807-809; doi:10.1021/cc800113d.
Lee et al., Accurate MALDI-TOF/TOF Sequencing of One-Bead-One-Compound Peptide Libraries with Application to the Identification of Multi-ligand Protein Affinity Agents Using in Situ Click Chemistry Screening, Anal Chem., Jan. 15, 2010, vol. 82, No. 2, pp. 672-679, doi:10.1021/ac902195y.
Leung et al., Cloning, expression, and primary structure of *Metapenaeus ensis* tropomyosin, the major heat-stable shrimp allergen, J Allergy Clin Immunol., vol. 94, No. 5, Nov. 1994, pp. 882-890.
Leung et al., High Throughput screening of mimotopes using OBOC combinatorial peptide library, EAACI Congress, Jun. 8, 2014, 13 pages.
Leung et al., IgE reactivity against a cross-reactive allergen in crustacea and mollusca: Evidence for tropomyosin as the common allergen, J Allergy Clin Immunol., Nov. 1996, vol. 98, No. 5, Part 1, pp. 954-961.
Leung et al., Induction of Shrimp Tropomyosin-Specific Hypersensitivity in Mice, Int Arch Allergy Immunol., 2008, vol. 147, pp. 305-314.
Leung et al., Screening and identification of mimotopes of the major shrimp allergen tropomyosin using one-bead-one compound peptide libraries, Cellular & Molecular Immunology, 2017, vol. 14, pp. 308-318.
Li et al., Induction of Th1-Type Immune Response by Chitosan Nanoparticles Containing Plasmid DNA Encoding House Dust Mite Allergen Der p 2 for Oral Vaccination in Mice, Cellular & Molecular Immunology, Feb. 2009, vol. 6, No. 1, pp. 45-50.
Miyamoto et al., Screening of an OBOC combinatorial library for beta-actin identifies molecules active toward Ramos B-lymphoma cells, Anal Biochem., Mar. 1, 2008, vol. 374, No. 1, pp. 112-120.
Myrset et al., Mapping of the Immunodominant Regions of Shrimp Tropomyosin Pan b 1 by Human IgE-Binding and IgE Receptor Crosslinking Studies, Int Arch Allergy Immunol., 2013, vol. 162, pp. 25-38.
Negi et al., Automated Detection of Conformational Epitopes Using Phage Display Peptide Sequences, Bioinformatics and Biology Insights, 2009, vol. 3, pp. 71-81.
Niall, Automated Edman Degradation: The Protein Sequenator, Addendum. Enzyme Structure, Part B-Sequence Determination, 1973, pp. 942-1010.
Pacios et al., Mimotope mapping as a complementary strategy to define allergen IgE-epitopes: Peach Prup 3 allergen as a model, Unidad de Quimicay Bioquimica, Departamento de Biotecnologia, E.T.S. Ingenieros de Montes, Madrid, Spain, 2008, 8 pages.
Peng et al., Development of a lipopolysaccharide targeted peptide mimic vaccine against Q fever, J Immunol., Nov. 15, 2012, vol. 189, No. 10, 27 pages; doi:10.4049/jimmunol.1201622.
Purohit et al., Role of tropomyosin as a cross-reacting allergen in sensitization to cockroach in patients from Martinique (French Caribbean island) with a respiratory allergy to mite and a food allergy to crab and shrimp, European Annals of Allergy and Clinical Immunology, Mar. 2007, vol. 39, No. 3, pp. 85-88.
Raveendra et al., Discovery of Peptoid Ligands for Anti-Aquaporin 4 Antibodies, Chem Biol., Mar. 21, 2013, vol. 20, No. 3, pp. 351-359.
Scholl et al., Phage-displayed Bet min 1, a mimotope of the major birch pollen allergen Bet v 1, induces B cell responses to the natural antigen using bystander T cell help, 2002, Clin. Exp Allergy, vol. 32, 2002, pp. 1583-1588.
Shafique et al., Group 10 allergens (tropomyosins) from house-dust mites may cause covariation of sensitization to allergens from other invertebrates, Fall 2012, vol. 3, No. 2, pp. e74-e90.
Sievers et al., Fast, scalable generation of high-quality protein multiple sequence alignments using Clustal Omega, Molecular Systems Biology, 2011, vol. 7, 6 pages.
Subbarayal et al., Kinetics, cross-reactivity, and specificity of Bet v 1—specific IgG4 antibodies induced by immunotherapy with birch pollen, Allergy, EAACI, 2013, vol. 68, pp. 1377-1386.
Szalai et al., Mimotopes identify conformational B-cell epitopes on the two major house dust mite allergens Der p 1 and Der p 2, Molecular Immunology, 2008, vol. 45, pp. 1308-1317.
Tiwari et al., Validation of a Phage Display and Computational Algorithm by Mapping a Conformational Epitope of Bla g 2, Int Arch Allergy Immunol., 2012, vol. 157, pp. 323-330.
Untersmayr et al., Mimotopes identify conformational epitopes on parvalbumin, the major fish allergen, Molecular Immunology, 2006, vol. 43, pp. 1454-1461.
Wai et al., Immunization with Hypoallergens of Shrimp Allergen Tropomyosin Inhibits Shrimp Tropomyosin Specific IgE Reactivity, Plos One, Nov. 2014, vol. 9, No. 11,10 pages.
Wallmann et al., Mimotope vaccination for therapy of allergic asthma: anti-inflammatory effects in a mouse model, Clinical & Experimental Allergy, 2010, vol. 40, pp. 650-658.
Wang et al., Correlation of specific IgE to shrimp with cockroach and dust mite exposure and sensitization in an inner city population, J Allergy Clin Immunol., Oct. 2011, vol. 128, No. 4, pp. 834-837.
Wang et al., Virus-like particles of hepatitis B virus core protein containing five mimotopes of infectious bursal disease virus (IBDV) protect chickens against IBDV, Vaccine, 2012, vol. 30, pp. 2125-2130.
Wheeler et al., A Th1-Inducing Adjuvant, MPL®, Enhances Antibody Profiles in Experimental Animals Suggesting It Has the Potential to Improve the Efficacy of Allergy Vaccines, Int Arch Allergy Immunol, 2001, vol. 126, pp. 135-139.
Zhong et al., Mimotopes selected with neutralizing antibodies against multiple subtypes of influenza A, Virology Journal, 2011, vol. 8:542,11 pages.

* cited by examiner

| Cluster | Sequence |
|---|---|
| Cluster 1 |     R I W V G H F M L<br>M R I M H L N W M Y W K |
| Cluster 2 | D I H E E S P D<br>    H D G I P D W S M |
| Cluster 3 | P T D V E R K T S Y T L<br>   T K Y E R G G R V R K I<br>K R L F E R D G |
| Cluster 4 |         K G H T K A H H G K N T<br>          G T K L Q H F R Q<br>V T W E R T T K H Q H W<br>       Y K T P H Q V F Q |
| Cluster 5 |           R T I P T M H W I H<br>      L H T I P V M I<br>I K A L S R L Q T I Y G |
| Cluster 6 |       T F V D D R R F M S<br>    H W S S T R R F P P<br>K L A Y M H V R V<br>    M H V L L M R R D |
| Cluster 7 | M V G W P P K H R K D K<br>   R P W P Q A H P N L |
| Non-Clustering | H W H A K H A Q R<br>W Q R H M V H T W R W M<br>A S S R W L G K V H D V<br>F F E A G F G N K<br>R A V F F R N D H |

*FIG. 1*

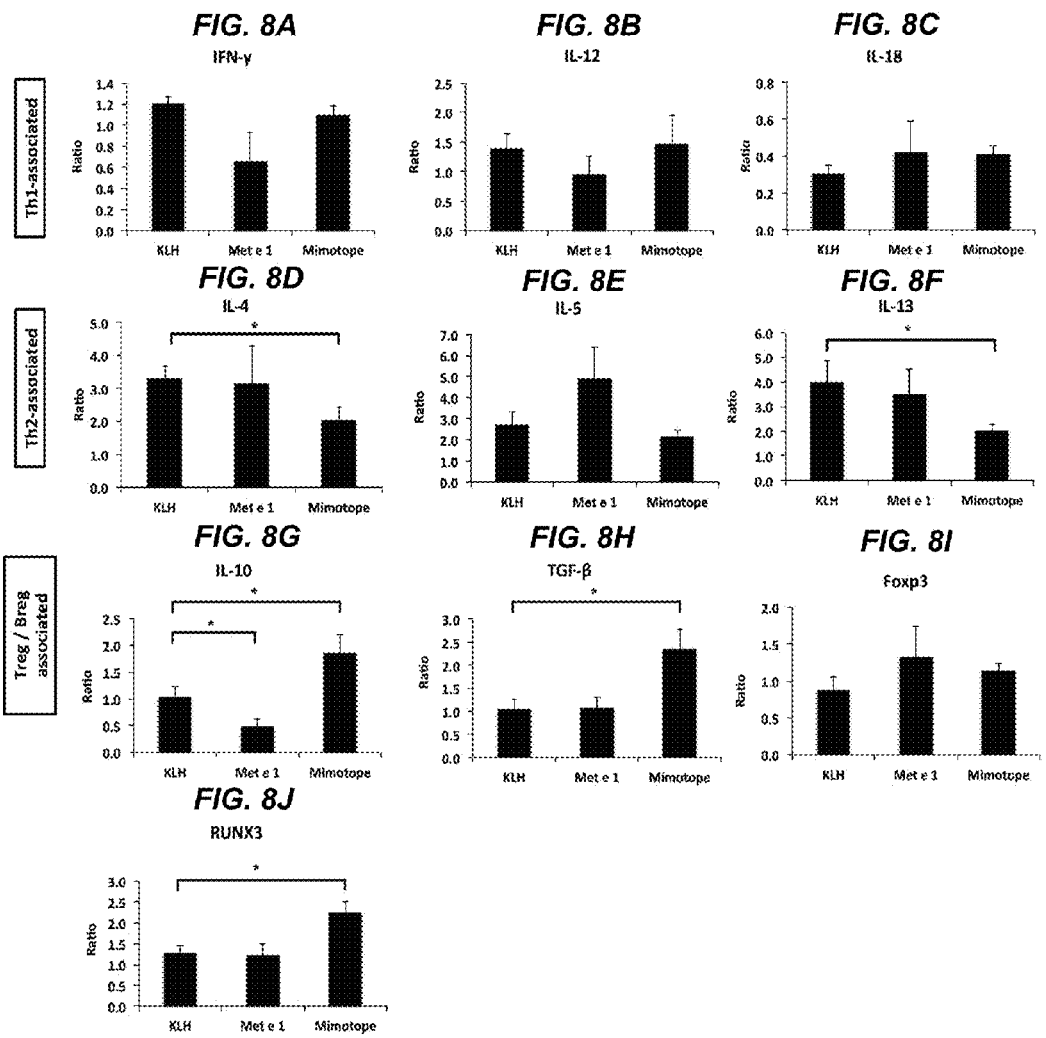

SEQUENCE LISTING

```
<160> NUMBER OF SEQ ID NOS: 47

<210> SEQ ID NO 1
<211> LENGTH: 9
<212> TYPE: PRT
<213> ORGANISM: Artificial Sequence
<220> FEATURE:
<223> OTHER INFORMATION: Cluster 1 mimotope

<400> SEQUENCE: 1

Arg Ile Trp Val Gly His Phe Met Leu
1               5

<210> SEQ ID NO 2
<211> LENGTH: 12
<212> TYPE: PRT
<213> ORGANISM: Artificial Sequence
<220> FEATURE:
<223> OTHER INFORMATION: Synthetic  Cluster 1 mimotope

<400> SEQUENCE: 2

Met Arg Ile Met His Leu Asn Trp Met Tyr Trp Lys
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Synthetic  Cluster 2 mimotope

<400> SEQUENCE: 3

Asp Ile His Glu Glu Ser Pro Asp
1               5

<210> SEQ ID NO 4
<211> LENGTH: 9
```

```
<212> TYPE: PRT
<213> ORGANISM: Artificial Sequence
<220> FEATURE:
<223> OTHER INFORMATION: Synthetic Cluster 2 mimotope

<400> SEQUENCE: 4

His Asp Gly Ile Pro Asp Trp Ser Met
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic Cluster 3 mimotope

<400> SEQUENCE: 5

Pro Thr Asp Val Glu Arg Lys Thr Ser Tyr Thr Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic Cluster 3 mimotope

<400> SEQUENCE: 6

Thr Lys Tyr Glu Arg Gly Gly Arg Val Arg Lys Ile
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Synthetic Cluster 3 mimotope

<400> SEQUENCE: 7

Lys Arg Leu Phe Glu Arg Asp Gly
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic Cluster 4 mimotope

<400> SEQUENCE: 8

Lys Gly His Thr Lys Ala His His Gly Lys Asn Thr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Synthetic Cluster 4 mimotope

<400> SEQUENCE: 9

Gly Thr Lys Leu Gln His Phe Arg Gln
1               5

<210> SEQ ID NO 10
<211> LENGTH: 12
<212> TYPE: PRT
```

```
<213> ORGANISM: Artificial Sequence
<220> FEATURE:
<223> OTHER INFORMATION: Synthetic Cluster 4 mimotope

<400> SEQUENCE: 10

Val Thr Trp Glu Arg Thr Thr Lys His Gln His Trp
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Cluster 4 mimotope

<400> SEQUENCE: 11

Tyr Lys Thr Pro His Gln Val Phe Gln
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Cluster 5 mimotope

<400> SEQUENCE: 12

Arg Thr Ile Pro Thr Met His Trp Ile His
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Synthetic Cluster 5 mimotope

<400> SEQUENCE: 13

Leu His Thr Ile Pro Val Met Ile
1               5

<210> SEQ ID NO 14
<211> LENGTH: 12
<212> TYPE: PRT
<213> ORGANISM: Artificial Sequence
<220> FEATURE:
<223> OTHER INFORMATION: Synthetic Cluster 5 mimotope

<400> SEQUENCE: 14

Ile Lys Ala Leu Ser Arg Leu Gln Thr Ile Tyr Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Cluster 6 mimotope

<400> SEQUENCE: 15

Thr Phe Val Asp Asp Arg Arg Phe Met Ser
1               5                   10

<210> SEQ ID NO 16
<211> LENGTH: 10
<212> TYPE: PRT
<213> ORGANISM: Artificial Sequence
```

```
<220> FEATURE:
<223> OTHER INFORMATION: Synthetic  Cluster 6 mimotope

<400> SEQUENCE: 16

His Trp Ser Ser Thr Arg Arg Phe Pro Pro
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthetic  Cluster 6 mimotope

<400> SEQUENCE: 17

Lys Leu Ala Tyr Met His Val Arg Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic  Cluster 6 mimotope

<400> SEQUENCE: 18

Met His Val Leu Leu Met Arg Arg Asp
1               5

<210> SEQ ID NO 19
<211> LENGTH: 12
<212> TYPE: PRT
<213> ORGANISM: Artificial Sequence
<220> FEATURE:
<223> OTHER INFORMATION: Synthetic  Cluster 7 mimotope

<400> SEQUENCE: 19

Met Val Gly Trp Pro Pro Lys His Arg Lys Asp Lys
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic  Cluster 7 mimotope

<400> SEQUENCE: 20

Arg Pro Trp Pro Gln Ala His Pro Asn Leu
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic  Non-clustering mimotope

<400> SEQUENCE: 21

His Trp His Ala Lys Asn Ala Gln Arg
1               5

<210> SEQ ID NO 22
<211> LENGTH: 12
<212> TYPE: PRT
<213> ORGANISM: Artificial Sequence
<220> FEATURE:
```

```
<223> OTHER INFORMATION: Synthetic  Non-clustering mimotope

<400> SEQUENCE: 22

Trp Gln Arg His Met Val His Thr Trp Arg Trp Met
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Synthetic  Non-clustering mimotope

<400> SEQUENCE: 23

Ala Ser Ser Arg Trp Leu Gly Lys Val His Asp Val
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Synthetic  Non-clustering mimotope

<400> SEQUENCE: 24

Phe Phe Glu Ala Gly Lys Gly Asn Lys
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic  Non-clustering mimotope

<400> SEQUENCE: 25

Arg Ala Val Phe Phe Arg Asn Asp His
1               5

<210> SEQ ID NO 26
<211> LENGTH: 274
<212> TYPE: PRT
<213> ORGANISM: Artificial Sequence
<220> FEATURE:
<223> OTHER INFORMATION: Synthetic  Predicted epitopes

<400> SEQUENCE: 26

Met Lys Leu Glu Lys Asp Asn Ala Met Asp Arg Ala Asp Thr Leu Glu
1               5                   10                  15

Gln Gln Asn Lys Glu Ala Asn Asn Arg Ala Glu Lys Ser Glu Glu Glu
            20                  25                  30

Val His Asn Leu Gln Lys Arg Met Gln Gln Leu Glu Asn Asp Leu Asp
        35                  40                  45

Gln Val Gln Glu Ser Leu Leu Lys Ala Asn Asn Gln Leu Val Glu Lys
    50                  55                  60

Asp Lys Ala Leu Ser Asn Ala Glu Gly Glu Val Ala Ala Leu Asn Arg
65                  70                  75                  80

Arg Ile Gln Leu Leu Glu Glu Asp Leu Glu Arg Ser Glu Glu Arg Leu
                85                  90                  95

Asn Thr Ala Thr Thr Lys Leu Ala Glu Ala Ser Gln Ala Ala Asp Glu
            100                 105                 110

Ser Glu Arg Met Arg Lys Val Leu Glu Asn Arg Ser Leu Ser Asp Glu
        115                 120                 125
```

```
Glu Arg Met Asp Ala Leu Glu Asn Gln Leu Lys Glu Ala Arg Phe Leu
        130                 135                 140

Ala Glu Glu Ala Asp Arg Lys Tyr Asp Glu Val Ala Arg Lys Leu Ala
145                 150                 155                 160

Met Val Glu Ala Asp Leu Glu Arg Ala Glu Glu Arg Ala Glu Thr Gly
                165                 170                 175

Glu Ser Lys Ile Val Glu Leu Glu Glu Leu Arg Val Val Gly Asn
                180                 185                 190

Asn Leu Lys Ser Leu Glu Val Ser Glu Glu Lys Ala Asn Gln Arg Glu
                195                 200                 205

Glu Ala Tyr Lys Glu Gln Ile Lys Thr Leu Thr Asn Lys Leu Lys Ala
        210                 215                 220

Ala Glu Ala Arg Ala Glu Phe Ala Glu Arg Ser Val Gln Lys Leu Gln
225                 230                 235                 240

Lys Glu Val Asp Arg Leu Glu Asp Glu Leu Val Asn Glu Lys Glu Lys
                245                 250                 255

Tyr Lys Ser Ile Thr Asp Glu Leu Asp Gln Thr Phe Ser Glu Leu Ser
                260                 265                 270

Gly Tyr

<210> SEQ ID NO 27
<211> LENGTH: 274
<212> TYPE: PRT
<213> ORGANISM: Metapenaeus ensis

<400> SEQUENCE: 27

Met Lys Leu Glu Lys Asp Asn Ala Met Asp Arg Ala Asp Thr Leu Glu
1               5                   10                  15

Gln Gln Asn Lys Glu Ala Asn Asn Arg Ala Glu Lys Ser Glu Glu Glu
                20                  25                  30

Val His Asn Leu Gln Lys Arg Met Gln Gln Leu Glu Asn Asp Leu Asp
            35                  40                  45

Gln Val Gln Glu Ser Leu Leu Lys Ala Asn Asn Gln Leu Val Glu Lys
        50                  55                  60

Asp Lys Ala Leu Ser Asn Ala Glu Gly Glu Val Ala Ala Leu Asn Arg
65                  70                  75                  80

Arg Ile Gln Leu Leu Glu Glu Asp Leu Glu Arg Ser Glu Glu Arg Leu
                85                  90                  95

Asn Thr Ala Thr Thr Lys Leu Ala Glu Ala Ser Gln Ala Ala Asp Glu
            100                 105                 110

Ser Glu Arg Met Arg Lys Val Leu Glu Asn Arg Ser Leu Ser Asp Glu
        115                 120                 125

Glu Arg Met Asp Ala Leu Glu Asn Gln Leu Lys Glu Ala Arg Phe Leu
        130                 135                 140

Ala Glu Glu Ala Asp Arg Lys Tyr Asp Glu Val Ala Arg Lys Leu Ala
145                 150                 155                 160

Met Val Glu Ala Asp Leu Glu Arg Ala Glu Glu Arg Ala Glu Thr Gly
                165                 170                 175

Glu Ser Lys Ile Val Glu Leu Glu Glu Leu Arg Val Val Gly Asn
                180                 185                 190

Asn Leu Lys Ser Leu Glu Val Ser Glu Glu Lys Ala Asn Gln Arg Glu
                195                 200                 205

Glu Ala Tyr Lys Glu Gln Ile Lys Thr Leu Thr Asn Lys Leu Lys Ala
        210                 215                 220
```

```
Ala Glu Ala Arg Ala Glu Phe Ala Glu Arg Ser Val Gln Lys Leu Gln
225                 230                 235                 240

Lys Glu Val Asp Arg Leu Glu Asp Glu Leu Val Asn Glu Lys Glu Lys
                245                 250                 255

Tyr Lys Ser Ile Thr Asp Glu Leu Asp Gln Thr Phe Ser Glu Leu Ser
            260                 265                 270

Gly Tyr

<210> SEQ ID NO 28
<211> LENGTH: 284
<212> TYPE: PRT
<213> ORGANISM: Penaeus monodon

<400> SEQUENCE: 28

Met Asp Ala Ile Lys Lys Met Gln Ala Met Lys Leu Glu Lys Asp
1               5                   10                  15

Asn Ala Met Asp Arg Ala Asp Thr Leu Glu Gln Gln Asn Lys Glu Ala
                20                  25                  30

Asn Asn Arg Ala Glu Lys Ser Glu Glu Val His Asn Leu Gln Lys
            35                  40                  45

Arg Met Gln Gln Leu Glu Asn Asp Leu Asp Gln Val Gln Glu Ser Leu
50                  55                  60

Leu Lys Ala Asn Ile Gln Leu Val Glu Lys Asp Lys Ala Leu Ser Asn
65                  70                  75                  80

Ala Glu Gly Glu Val Ala Ala Leu Asn Arg Arg Ile Gln Leu Leu Glu
                85                  90                  95

Glu Asp Leu Glu Arg Ser Glu Arg Leu Asn Thr Ala Thr Thr Lys
                100                 105                 110

Leu Ala Glu Ala Ser Gln Ala Ala Asp Glu Ser Glu Arg Met Arg Lys
            115                 120                 125

Val Leu Glu Asn Arg Ser Leu Ser Asp Glu Glu Arg Met Asp Ala Leu
            130                 135                 140

Glu Asn Gln Leu Lys Glu Ala Arg Phe Leu Ala Glu Glu Ala Asp Arg
145                 150                 155                 160

Lys Tyr Asp Glu Val Ala Arg Lys Leu Ala Met Val Glu Ala Asp Leu
                165                 170                 175

Glu Arg Ala Glu Glu Arg Ala Glu Thr Gly Glu Ser Lys Ile Val Glu
            180                 185                 190

Leu Glu Glu Glu Leu Arg Val Val Gly Asn Asn Leu Lys Ser Leu Glu
            195                 200                 205

Val Ser Glu Glu Lys Ala Asn Gln Arg Glu Glu Ala Tyr Lys Glu Gln
            210                 215                 220

Ile Lys Thr Leu Thr Asn Lys Leu Lys Ala Ala Glu Ala Arg Ala Glu
225                 230                 235                 240

Phe Ala Glu Arg Ser Val Gln Lys Leu Gln Lys Glu Val Asp Arg Leu
                245                 250                 255

Glu Asp Glu Leu Val Asn Glu Lys Glu Lys Tyr Lys Ser Ile Thr Asp
            260                 265                 270

Glu Leu Asp Gln Thr Phe Ser Glu Leu Ser Gly Tyr
            275                 280

<210> SEQ ID NO 29
<211> LENGTH: 11
<212> TYPE: PRT
<213> ORGANISM: Artificial Sequence
```

```
<220> FEATURE:
<223> OTHER INFORMATION: Synthetic Bet v 1 allergen

<400> SEQUENCE: 29

Cys Gln Gln Thr Leu Ser Val Arg Ala Leu Cys
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic Bet v 1 allergen

<400> SEQUENCE: 30

Cys Gly Gly Thr Pro Pro Ser Leu Pro Thr Cys
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic Bet v 1 allergen

<400> SEQUENCE: 31

Cys Gly Gly Thr Arg Arg Pro Ile Ala Ser Cys
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic Der p 1 allergen

<400> SEQUENCE: 32

Lys Gly Ile Pro Asn Thr Lys Ala Pro
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Der p 1 allergen

<400> SEQUENCE: 33

Gly Ile Arg Glu Val Trp Pro Ala Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Der p 1 allergen

<400> SEQUENCE: 34

Lys Gly Thr Thr Gly Val Arg Asn Thr
1               5

<210> SEQ ID NO 35
<211> LENGTH: 9
<212> TYPE: PRT
<213> ORGANISM: Artificial Sequence
<220> FEATURE:
```

<223> OTHER INFORMATION: Synthetic Der p 2 allergen

<400> SEQUENCE: 35

Phe Val Val Glu Tyr Thr Lys Lys Trp
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic Der p 2 allergen

<400> SEQUENCE: 36

Ser Trp Trp Asn Leu Pro Gln Ile Gly
1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic Der p 2 allergen

<400> SEQUENCE: 37

Lys Gly Ile Thr Thr Lys Trp Met Ala
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic Der p 2 allergen

<400> SEQUENCE: 38

Ala Gly Ile Ser Tyr Thr Lys Thr Trp
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic Bla g 2 allergen

<400> SEQUENCE: 39

Ser Met Met Lys Ala Asp Phe Asp Glu Glu Pro Arg
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Synthetic Bla g 2 allergen

<400> SEQUENCE: 40

Ser Met Met Lys Ala Asp Phe Glu Glu Glu Pro Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic Parvalbumin allergen -continued

```
<400> SEQUENCE: 41

Cys Tyr Arg Gly Val Thr Leu Ala Gly His Arg Cys
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Synthetic   Parvalbumin allergen

<400> SEQUENCE: 42

Cys Phe Lys Gly Val Arg Leu Asp Gly Thr Pro Cys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic   Parvalbumin allergen

<400> SEQUENCE: 43

Cys Tyr Arg Gly Ala Arg Val Asp Gly Leu Met Cys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Synthetic   Pru p 3 allergen
<220> FEATURE:
<221> NAME/KEY: VARIANT
<222> LOCATION: (11)..(11)
<223> OTHER INFORMATION: Xaa = any amino acid

<400> SEQUENCE: 44

Pro Ser Arg Thr Pro Arg Pro Glu Trp Ala Xaa Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Synthetic   Pru p 3 allergen

<400> SEQUENCE: 45

Thr Ser Arg Pro Ala Leu Leu Asn Asp Gln Gly His
1               5                   10

<210> SEQ ID NO 46
<211> LENGTH: 9
<212> TYPE: PRT
<213> ORGANISM: Artificial Sequence
<220> FEATURE:
<223> OTHER INFORMATION: Synthetic   Non-clustering mimotope

<400> SEQUENCE: 46

His Trp His Ala Lys His Ala Gln Arg
1               5

<210> SEQ ID NO 47
<211> LENGTH: 9
<212> TYPE: PRT
```

```
<213> ORGANISM: Artificial Sequence
<220> FEATURE:
<223> OTHER INFORMATION: Synthetic Non-clustering mimotope

<400> SEQUENCE: 47

Phe Phe Glu Ala Gly Phe Gly Asn Lys
1               5
```

MIMOTOPES OF TROPOMYOSIN FOR USE IN IMMUNOTHERAPY FOR SHELLFISH AND/OR ARTHROPOD ALLERGY

CROSS-REFERENCES TO RELATED APPLICATIONS

This application claims priority to U.S. Provisional Application No. 62/171,681, filed Jun. 5, 2015, the disclosure of which is hereby incorporated by reference in its entirety for all purposes.

REFERENCE TO A SEQUENCE LISTING

The Sequence Listing written in file SubstituteSequence-Listing_070772-1012190.txt created on Jun. 21, 2017, 17,192 bytes, machine format IBM-PC, MS-Windows operating system, is hereby incorporated by reference in its entirety for all purposes.

BACKGROUND OF THE INVENTION

More than 25% of the population suffer from IgE-mediated allergies, which can involve symptoms ranging from milder ones such as hay fever to serious episodes of asthma or anaphylactic shock. These allergies may be due to environmental allergens such as pollens, mites, insects, and the like, or food allergens such as peanuts, shellfish, eggs, milk, wheat, tree nuts, and the like. Exposure to an allergen following allergic sensitization (e.g., the initial exposure to the allergen and subsequent induction of allergen-specific IgE antibodies) leads to cross-linking of the allergen specific-IgE antibodies bound to the surface of mast cells and basophils, degranulation of these cells, and release of inflammatory mediators, proteases, and pro-inflammatory cytokines that lead to the symptoms associated with early or acute allergic reactions.

Pharmaceutical treatment of allergy has focused on mitigation of allergic inflammation and often provides only temporary relief to the individual. Allergen-specific immunotherapy (SIT), on the other hand, is designed to provide long-last effects by modifying the individual's allergen-specific immune response. SIT is based on the repeated administration of a specific allergen to the individual over a period of time, e.g., years, such that the individual becomes desensitized to the allergen and can tolerate higher doses of the allergen without developing an allergic reaction. SIT involves the induction of antibodies against a specific allergen which block, and not enhance an allergic reaction. Traditional allergen-specific immunotherapy involves administration of allergen extracts or recombinant allergens which can cause side effects such as inflammatory response and anaphylactic reactions. In addition, traditional SIT is time consuming and often fails to achieve its goal of desensitizing the individual to the Allergan.

Allergies to shellfish, e.g., shrimp, lobster, oysters, etc., are one of the most common food allergies. The major allergen in shrimp is an invertebrate tropomyosin protein. At least 80% of shrimp-allergic subjects react to tropomyosin and the protein binds approximately 85% of the shrimp-specific IgE from shrimp-allergic subjects. Recent studies have shown that tropomyosin is a cross-reactive allergen and is found in other crustaceans such as lobster, crab, squid, snail and oyster, as well as other invertebrates such as the house dust mite and cockroach (Ayuso et al., Int Arch Allergy Immunol, 2002, 129:38-48). A strong positive correlation has been established between IgE-mediated sensitization to shrimp, cockroach and dust mite (Wang et al., J Allergy Clin Immunol, 2011, 128(4):834-7; Shafique et al., Allergy Rhinol, 2012, 3:e74-e90).

There remains a need in the art for novel and efficacious therapies for allergies to invertebrate tropomyosins. The present invention satisfies this need and provides additional advantages as well.

BRIEF SUMMARY OF THE INVENTION

Provided herein is an isolated peptide having at least about 80% sequence identity to any one of SEQ ID NOS: 1-25. In some embodiments, the peptide has at least about 85%, 90%, or 95% sequence identity to any one of SEQ ID NOS:1-25. In some embodiments, the peptide comprises at least 8, 9, 10, 11, or 12 contiguous amino acids of any one of SEQ ID NOS:1-25. In some instances, the peptide comprises an amino acid sequence of any one of SEQ ID NOS:1-25. In some embodiments, the peptide is a mimotope of an epitope of a tropomyosin protein. The tropomyosin protein can be Met e 1 from *Metapenaeus ensis*. In some cases, the peptide induces antibodies against the tropomyosin protein. In particular embodiments, the peptide is not SEQ ID NO:7 or SEQ ID NO:12. In some embodiments, the peptide is from about 8 to about 25 amino acids in length. In other embodiments, the peptide is from about 8 to about 12 amino acids in length. The peptide can include an amino acid sequence consisting of any one of SEQ ID NOS:1-25. In some embodiments, the peptide is conjugated to a carrier protein. In some instances, the carrier protein is keyhole limpet hemocyanin (KLH).

Also provided herein is a composition comprising any one of the peptides described herein. In some embodiments, the composition comprises a plurality of the peptides described herein. For example, the plurality of the peptides can include at least 2, 3, 4, 5, 6, 7, 8, 9, 10, 11, 12, 13, 14, 15, 16, 17, 18, 19, 20, 21, 22, 23, 24 or 25 different peptides provided herein. The compositions can also include a pharmaceutically acceptable carrier.

In another aspect, provided herein is a kit comprising any one of the peptides described herein or a plurality thereof. In some embodiments, the plurality of the peptides can include at least 2, 3, 4, 5, 6, 7, 8, 9, 10, 11, 12, 13, 14, 15, 16, 17, 18, 19, 20, 21, 22, 23, 24 or 25 different peptides provided herein. The kit can also include instructions for use.

Also provided herein is an isolated nucleic acid comprising a nucleotide sequence encoding any one of the peptides described herein. In some embodiments, the nucleic acid is operably linked to an expression sequence and/or a control sequence. In some cases, the nucleic acid is incorporated into a vector, e.g., an expression vector.

In another aspect, provided herein is a composition comprising any one of the nucleic acids described herein or a plurality thereof. In some embodiments, the plurality of nucleic acids comprises at least 2, 3, 4, 5, 6, 7, 8, 9, 10, 11, 12, 13, 14, 15, 16, 17, 18, 19, 20, 21, 22, 23, 24, or 25 different nucleic acids described herein. The compositions can also include a pharmaceutically acceptable carrier.

In yet another aspect, provided herein is a kit comprising any one of the nucleic acids described herein or a plurality thereof. In some embodiments, the plurality of nucleic acids comprises at least 2, 3, 4, 5, 6, 7, 8, 9, 10, 11, 12, 13, 14, 15, 16, 17, 18, 19, 20, 21, 22, 23, 24, or 25 different nucleic acids described herein. The kit can also include instructions for use.

In some aspects, provided herein is a method for inducing antibodies against a tropomyosin protein from shellfish in a subject. The method comprises administering to the subject an effective amount of a peptide, a nucleic acid, or a composition disclosed herein. In other aspects, provided herein is a method for preventing, alleviating, or modulating hypersensitivity to shellfish in a subject. The method comprises administering to the subject an effective amount of a peptide, a nucleic acid, or a composition disclosed herein. In another aspect, provided herein is a method developing tolerance or desensitization to a tropomyosin protein from shellfish in a subject. The method comprises administering to the subject an effective amount of a peptide, a nucleic acid, or a composition disclosed herein. The shellfish can be a crustacean, mollusk, or echinoderm. In some cases, the crustacean is selected from the group consisting of crabs, lobsters, crayfish, shrimp, krill, and barnacles. In some instances, the mollusk is selected from the group consisting of clams, oysters, scallops, geoducks, mussels, squid, abalone, cuttlefish, and octopus. The echinoderm may be selected from the group consisting of starfish, sea urchin, and sea cucumber. In some embodiments, the subject has a shellfish allergy or is susceptible to developing a shellfish allergy. In some instances, the peptide or composition is administered orally, sublingually, intraperitoneally, intravenously, intramuscularly, intranasally, epicutaneously, or subcutaneously.

In other aspects, provided herein is a method for inducing antibodies against a tropomyosin protein from an arthropod in a subject. The method comprises administering to the subject an effective amount of a peptide, a nucleic acid, or a composition disclosed herein. In other aspects, provided herein is a method for preventing, alleviating, or modulating hypersensitivity to an arthropod in a subject. The method comprises administering to the subject an effective amount of a peptide, a nucleic acid, or a composition disclosed herein. In another aspect, provided herein is a method developing tolerance or desensitization to a tropomyosin protein from an arthropod in a subject. The method comprises administering to the subject an effective amount of a peptide, a nucleic acid, or a composition disclosed herein. The arthropod may be a house dust mite or a cockroach. In some embodiments, the subject has an allergy to an arthropod or is susceptible to developing an allergy to an arthropod. The peptide or composition may be administered orally, sublingually, intraperitoneally, intravenously, intramuscularly, intranasally, epicutaneously, or subcutaneously.

Other objects, features, and advantages of the present invention will be apparent to one of skill in the art from the following detailed description and figures.

BRIEF DESCRIPTION OF THE DRAWINGS

FIG. 1 shows that mimotopes sharing at least three identical amino acid residues at the same position were clustered into a group after multiple alignments by Clustal Omega. Twenty mimotopes were divided into seven clusters, with 2-4 mimotopes each. The clustering of mimotopes is not related to the serum pool used for screening. The sequences shown within each cluster are as follows (from top to bottom): Cluster 1: SEQ ID NOS:1 and 2; Cluster 2: SEQ ID NOS:3 and 4; Cluster 3: SEQ ID NOS:5, 6, and 7; Cluster 4: SEQ ID NOS:8, 9, 10, and 11; Cluster 5: SEQ ID NOS:12, 13, and 14; Cluster 6: SEQ ID NOS:15, 16, 17, and 18; and Cluster 7: SEQ ID NOS:19 and 20. Five "non-clustering" mimotopes from top to bottom: SEQ ID NOS: 46, 22, 23, 47, and 25) could not be grouped with any of the clusters and thus were not included for epitope mapping in this study.

FIG. 2A shows IgG1 and IgG2a levels of immunized mice (mean+SEM). All six groups of mice immunized with mimotope conjugates have a significantly higher IgG1 level compared to the control groups immunized with KLH alone or Der p 1 mimotope (p<0.05). No significant increase in IgG2a levels was observed. FIG. 2B shows IgG1 titer of mimotope-immunized mice from serum dilution of 1:100 to 1:1600. Met e 1-specific IgG1 was detected up to 1:1600 for the mimotope DIHEESPD (SEQ ID NO:3). Cluster 1 RIWVGHFML (SEQ ID NO:1); cluster 2 DIHEESPD (SEQ ID NO:3); cluster 3 KRLFERDG (SEQ ID NO:7); cluster 4 GTKLQHFRQ (SEQ ID NO:9); cluster 5 LHTIPVMI (SEQ ID NO:13); cluster 6 KLAYMHVRV (SEQ ID NO:17); and KGIPNTKAP (SEQ ID NO: 29).

FIG. 3A shows five major epitopes of Pen a 1 identified by Ayuso et al. (*Int Arch Allergy Immunol* 2002; 127, 27-3). FIG. 3B shows nine epitopes of Met e 1 identified by Wai et al. (*PLoS One* 2014; 9, e111649). FIG. 3C shows the predicted epitopes based on Met e 1 mimotopes using the EpiSearch program. FIG. 3D shows the predicted epitopes based on six sets of mimotopes from irrelevant allergens. The predicted epitopes using mimotopes as input overlap with 83% of both Pen a 1 epitopes, while predicted epitopes using irrelevant allergens overlap with a single epitope (16%) from Met e 1 (Met e 125-30) and none from Pen a 1.

In FIG. 5A, the arrow indicates a positive bead stained in blue. The positive bead can be easily distinguished from the others that remain transparent. FIG. 5B shows that the positive beads can be removed with a pipette under the microscope.

FIGS. 8A-8J illustrate a decrease in the expression levels of the pro-inflammatory cytokine genes IL-4 and IL-13 and up-regulation of the regulatory cytokine genes IL-10 and TGF-β in the mimotope-immunized mice described above after challenge with a tropomyosin allergen.

DETAILED DESCRIPTION OF THE INVENTION

I. Introduction

Figure 2A:
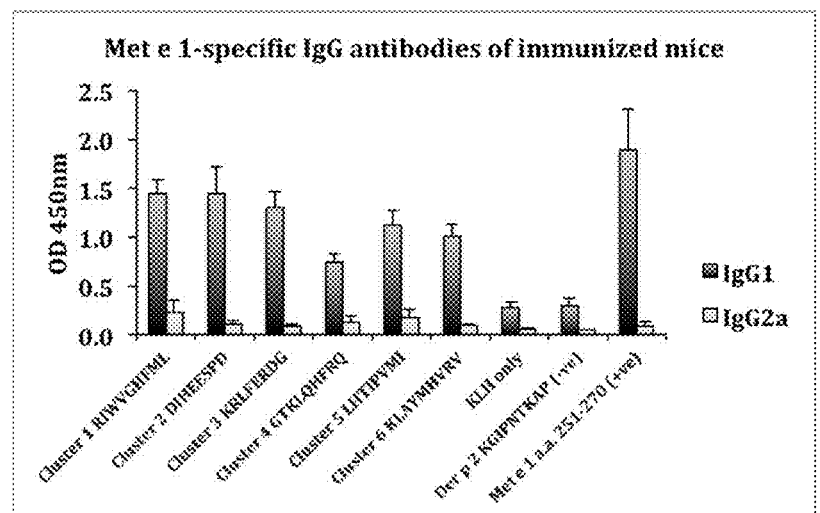
FIGS. 2A and 2B provide serum profiles of BALB/c mice (n=4) immunized with mimotopes conjugated to the carrier protein KLH. Mimotope KGIPNTKAP (SEQ ID NO: 29) of Der p 1 and an IgE binding epitope of Met e 1 (a.a. 251-270) were included as negative and positive controls, respectively. Results are expressed as mean optical density at 450 nm.
Figure 2B:
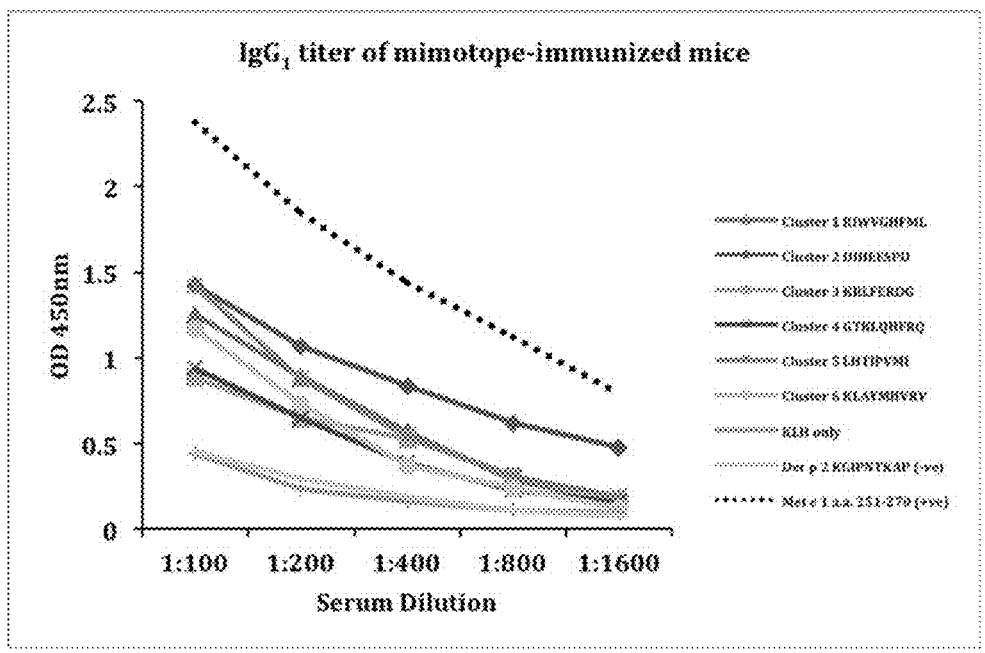

Provided herein are short peptides that mimic an epitope (e.g., mimotope) of an antigen. When coupled to a carrier protein for immunization, mimotopes have the capacity to induce antibodies, such as blocking antibodies, e.g., IgG and/or IgA class, against the corresponding native antigenic epitopes. A key advantage of mimotopes is that they are too short to crosslink IgE on mast cells and are devoid of allergen-specific T-cell epitopes, thereby minimizing the risk of anaphylactic side effects and late-phase T-cell mediated inflammation.

The peptide sequences described herein are based on a major shellfish allergen, tropomyosin from the shrimp species *Metapenaeus ensis* (Met e 1). The inventors have made the surprising discovery that upon conjugation to the carrier protein keyhole limpet hemocyanin (KLH), the peptides function as mimotopes to induce Met e 1-specific antibodies. As such, the peptides provided herein are useful for specific immunotherapy (SIT) against allergies induced by tropomyosin allergens.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "peptide," "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including peptides (i.e., epitopes), wherein the amino acid residues are linked by covalent peptide bonds.

The term "amino acid" includes naturally-occurring α-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Unnatural (non-naturally occurring) amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups or modified peptide backbones, e.g., homoserine, norleucine, methionine sulfoxide, methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins,* 1993).

The term "amino acid modification" or "amino acid alteration" refers to a substitution, a deletion, or an insertion of one or more amino acids.

The term "nucleic acid," "nucleotide" or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991), Ohtsuka et al., *J. Biol. Chem.* 260:2605-2608 (1985), and Rossolini et al., *Mol. Cell. Probes* 8:91-98 (1994)). The term nucleic acid is used interchangeably with gene, cDNA, and mRNA encoded by a gene.

The term "nucleotide sequence encoding a peptide" or "gene" means the segment of DNA involved in producing a peptide chain, it includes regions preceding and following the coding region (leader and trailer) involved in the transcription/translation of the gene product and the regulation of the transcription/translation, as well as intervening sequences (introns) between individual coding segments (exons).

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "percent identity" or "percent sequence identity," in the context of describing two or more polynucleotide or amino acid sequences, refer to two or more sequences or subsequences that are the same or have a specified percentage of amino acid residues or nucleotides that are the same (for example, a variant of a peptide of interest (e.g., mimotope of interest) used in the method of this invention has at least 80% sequence identity, preferably 85%, 90%, 91%, 92%, 93, 94%, 95%, 96%, 97%, 98%, 99%, or 100% identity, to a reference sequence, e.g., a corresponding epitope or mimotope of interest), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 8 amino acids in length, or more preferably over a region that is at least 8-25 or at least 8 to 12 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Additional examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see, e.g., Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA*, 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or peptides are substantially identical is that the peptide encoded by the first nucleic acid is immunologically cross reactive with the antibodies raised against the peptide encoded by the second nucleic acid. Thus, a peptide is typically substantially identical to a second peptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "vector" or "recombinant expression vector" refers a nucleic acid construct, generated recombinantly or synthetically, with a series of specified nucleic acid elements that permit transcription of a particular polynucleotide sequence in a host cell. An expression vector may be part of a plasmid, viral genome, or nucleic acid fragment. Typically, an expression vector includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. The term "promoter" is used herein to refer to an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. Other elements that may be present in an expression vector include those that enhance transcription (e.g., enhancers) and terminate transcription (e.g., terminators), as well as those that confer certain binding affinity or antigenicity to the recombinant peptide or protein produced from the expression vector.

The term "allergen" refers not only to naturally occurring allergen extracts and allergen molecules but also to mutants of allergens, hypoallergens or parts of allergen molecules, such as mimotopes, e.g., peptides. Mimotopes can likewise be peptides, such as peptides with an amino acid sequence length of at least about 8 to about 25 amino acids or more. Allergens are able to trigger an allergy, that is, an immediate-type hypersensitivity reaction, which is induced by the synthesis of IgE antibodies. Hypoallergens are natural or recombinant derivatives (e.g., mimotopes) of an allergen molecule which, due to slight differences compared with the amino acid sequence of the allergen, assume a conformation by which IgE-binding properties are lost.

The term "epitope" refers to a binding site including an amino acid motif (e.g., a linear amino acid sequence or a particular three dimensional structure) which can be bound by an immunoglobulin (e.g., IgE, IgG, etc.) or recognized by a T-cell receptor when presented by an APC in conjunction within the major histocompatibility complex (MHC).

The term "mimotope" refers to a compound or macromolecule, e.g., peptide that mimics the structure of an epitope and provokes an antibody response to the molecule it mimics. The compound may be of the same or of a different type of molecule as the original epitope.

The term "tropomyosin protein" refers to a protein belonging to a family of highly conserved proteins with multiple isoforms found in muscle and nonmuscle cells of all species of vertebrates and invertebrates. The native structure of a tropomyosin protein includes two parallel alpha-helical tropomyosin molecules that form a coiled-coil dimer. Allergenic tropomyosins are found in invertebrates such as crustaceans (e.g., shrimp, lobster, crab, and crawfish), arachnids (house dust mites, ticks), insects (e.g., cockroaches), and mollusks (e.g., squid, oysters, clams, mussels, cuttlefish, octopus, starfish, sea urchins, and the like). Due to a high degree of sequence homology among tropomyosin proteins from various species, these proteins are considered pan allergens and in some cases, can induce cross-reactive allergic reactions. Non-limiting examples of allergenic tropomyosin proteins includes those found in, e.g., shrimp (Met e 1 and Pen a 1), lobster (Pan s 1 and Hom a 1), crab (Cha f 1), squid (Tod p 1), snail (Tur c 1), oyster (Cra g 1), house dust mites (Der f 10 and Der p 10) and cockroaches (Per a7 and Bla g 7).

The term "Met e 1" refers to a *Metapenaeus ensis* (shrimp) tropomyosin allergen. Serum antibodies from patients with a shrimp allergy may exhibit positive IgE reactivity by, for example, immunoblotting to a Met e 1 tropomyosin protein. The *Metapenaeus ensis* tropomyosin (Met e 1) polypeptide sequence is set forth in, e.g., UniProt No. Q25456 and EMBL Accession No. AAA60330. The *Metapenaeus ensis* tropomyosin (Met e 1) mRNA (coding) sequence is set forth in, e.g., EMBL Accession No. U08008.

The term "carrier protein," "immunogenic carrier" or immunogenic carrier protein" refers to those materials which have the property of independently eliciting an immunogenic response in a host animal and which can be covalently coupled to a peptide either directly via formation of peptide or ester bonds between free carboxyl, amino or hydroxyl groups in the peptide and corresponding groups on the immunogenic carrier material, or alternatively by bonding through a conventional bifunctional linking group, or as a fusion protein.

Examples of such carriers include: albumins, such as BSA; globulins; thyroglobulins; hemoglobins; hemocyanins (particularly Keyhole Limpet Hemocyanin (KLH)); proteins extracted from *ascaris*, e.g. *ascaris* extracts such as those described in *J. Immun.*, 1973, 111: 260-268; *J. Immun.*, 1979, 122:302-308, *J. Immun.*, 1967, 98: 893-900; *Am. J. Physiol.*, 1960, 199:575-578 or purified products thereof; polylysine; polyglutamic acid; lysine-glutamic acid copolymers; copolymers containing lysine or ornithine; etc. Vaccines have been produced using diphtheria toxoid or tetanus toxoid as immunogenic carrier material (Lepow et al., *J. of Infectious Diseases*, 1984, 150:402-406; Coen Beuvery, E. et al., *Infection and Immunity*, 1983, 4:39-45) and these toxoid materials can also be used in the present invention.

The term "shellfish" refers to aquatic invertebrates with an exoskeleton that are consumed by humans. The term shellfish includes members of the phylum Arthropoda, class or subphylum Crustacea, such as shrimp, prawns, crab, lobster, crawfish, and barnacles; the phylum Mollusca, such as oysters, mussels, scallops, clams, geoducks, abalone, whelk, conch, squid, octopus, cuttlefish, and nautilus; and the phylum Echinodermata, such as sea urchins, starfish, and sea cucumbers.

The term "arthropod" refers to an invertebrate animal belong to the phylum Arthropoda including those of the three subphyla Chelicerata, Crustacea, and Uniramia. The term "arthropod" includes crustaceans, insects, arachnids, and the like.

The phrase "inducing antibodies against a tropomyosin protein" refers to generating or producing antibodies that specifically bind to a tropomyosin protein (anti-tropomyosin antibodies). In some embodiments of allergen immunotherapy or hyposensitization, antibodies such as IgG and/or IgA class are generated/produced by the subject and can block the binding of allergen-specific IgE antibodies (e.g., anti-tropomyosin IgE antibodies) to the allergen (e.g., the allergenic tropomyosin protein) in the subject.

The phrase "allergic reaction" or "allergic response" refers to an immune response that is IgE mediated with clinical symptoms primarily involving the cutaneous (e.g., urticaria, angioedema, pruritus), respiratory (e.g., wheezing, coughing, laryngeal edema, rhinorrhea, watery/itching eyes), gastrointestinal (e.g., vomiting, abdominal pain, diarrhea) and cardiovascular (e.g., systemic vasodilation, hypotension) systems, and any combination thereof.

The phrase "preventing, alleviating, or modulating hypersensitivity to" an allergen refers to reducing, decreasing, minimizing or eliminating an allergic response to a specific allergen upon exposure to the allergen, or providing preexposure prophylaxis to prevent an IgE-mediated allergic reaction (e.g., a hypersensitivity reaction). In some cases, the phrase includes inducing hyposensitivity or desensitization to the allergen.

The phrase "developing tolerance to a tropomyosin protein" refers to developing immunity or immune tolerance for an allergenic tropomyosin protein in a subject, which may reduce the risk of having an allergic reaction to the tropomyosin allergen.

The terms "treat," "treating" and "treatment" refer to the administering of a therapeutically effective anti-inflammatory amount of the peptide, nucleic acid, or a pharmaceutical composition comprising same which is effective to ameliorate undesired symptoms associated with inflammation, to prevent the manifestation of such symptoms before they occur, to slow down the progression of an inflammatory condition, to slow down the deterioration of symptoms associated with an inflammatory condition, to slow down the irreversible damage caused by the chronic stage of an inflammatory condition, to lessen the severity or cure an inflammatory condition, to improve survival rate or more rapid recovery form such a condition. It should be noted that in the context of the present invention the term "treatment" also denotes "prophylactic treatment", i.e. for prevention of the development of an inflammatory condition or to prevent the re-occurrence of an acute inflammatory phase in a chronic individual. To this end, the molecule may be administered to individuals who do not have inflammation and especially, to individuals having a high-risk of developing an inflammatory condition, e.g. as a result of exposure to an infecting agent or allergen. In this case, the molecule will typically be administered over an extended period of time in a single daily dose (e.g. to produce a cumulative effective amount), in several doses a day, as a single dose for several days, etc. so as to prevent the manifestation of inflammation.

The term "administering" or "administration" of a therapeutic peptide, nucleic acid or composition to a subject includes oral administration, topical contact, administration as a suppository, intravenous, intraperitoneal, intramuscular, intralesional, intrathecal, intranasal, or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, epicutaneous, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a peptide of the invention for preventing or relieving one or more symptoms associated with the presence or activity of maternal antibodies. By "co-administer" it is meant that a peptide of the invention is administered at the same time, just prior to, or just after the administration of a second drug.

The term "pharmaceutically acceptable carrier" refers to a substance that aids the administration of an active agent to a cell, an organism, or a subject. "Pharmaceutically acceptable carrier" refers to a carrier or excipient that can be included in the compositions of the invention and that causes no significant adverse toxicological effect on the patient. Non-limiting examples of pharmaceutically acceptable carrier include water, NaCl, normal saline solutions, lactated Ringer's, normal sucrose, normal glucose, binders, fillers, disintegrants, lubricants, coatings, sweeteners, flavors and colors, liposomes, dispersion media, microcapsules, cationic lipid carriers, isotonic and absorption delaying agents, and the like. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc. In some instances, the carrier is an agent that facilitates the delivery of the amino acid molecule to a target cell or tissue. One of skill in the art will recognize that other pharmaceutical carriers are useful in the present invention.

The term "effective amount" or "sufficient amount" refers to the amount of a peptide, nucleic acid, or composition that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The specific amount may vary depending on one or more of: the particular agent chosen, the target cell type, the location of the target cell in the subject, the dosing regimen to be followed, whether it is administered in combination with other compounds, timing of administration, and the physical delivery system in which it is carried.

For the purposes herein an effective amount is determined by such considerations as may be known in the art. The amount must be effective to achieve the desired anti-inflammatory effect in a subject suffering from an inflammatory state, the desired anti-inflammatory effect include, for example, amelioration of undesired symptoms associated with inflammation, prevention of the manifestation of such symptoms before they occur, slowing down progression of an inflammatory condition, slowing down the deterioration of symptoms associated with an inflammatory condition, slowing down any irreversible damage caused by a chronic stage of an inflammatory condition, lessening of the severity or curing an inflammatory condition, improving survival rate or providing more rapid recovery form such a condition. Further, in the context of prophylactic treatment the amount may also be effective to prevent the development of an inflammatory condition.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule to the corresponding receptor, its distribution profile within the body, a variety of pharmacological parameters such as half-life in the body, on undesired side effects, if any, on factors such as age and gender, etc.

III. Detailed Description of the Embodiments

A. Isolated Peptides

The present disclosure provides an isolated peptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the amino acid sequences set forth in SEQ ID NOS: 1-25 or Table 2. In some embodiments, the peptide comprises an amino acid sequence comprising or consisting of any one of the sequences as set forth in SEQ ID NOS:1-25 or Table 2. In other embodiments, the isolated peptide has 100% sequence identity to any one of the amino acid sequences set forth in SEQ ID NOS: 1-25 or Table 2. In another embodiment, the isolated peptide comprises an amino acid sequence of any one as set forth in SEQ ID NOS: 1-25 or Table 2. In yet another embodiment, the isolated peptide comprises an amino acid sequence consisting of any one as set forth in SEQ ID NOS: 1-25 or Table 2. In some cases, the peptide is not the peptide as set forth in SEQ ID NO: 7 or SEQ ID NO: 12.

In some embodiments, the peptide comprises at least 8, 9, 10, 11 or 12 contiguous amino acids of any one of the amino acid sequences set forth in SEQ ID NOS: 1-25 or Table 2. In other embodiments, the peptide comprises an amino acid sequence comprising or consisting of at least 8, 9, 10, 11 or 12 contiguous amino acids as set forth in SEQ ID NOS: 1-25 or Table 2.

In some embodiments, the peptide is between about 8 to about 25 amino acids in length, between about 8 to about 25 amino acids in length, between about 8 to about 20 amino acids in length, between about 8 to about 15 amino acids in length, between about 8 to about 12 amino acids in length, between about 10 to about 25 amino acids in length, between about 10 to about 20 amino acids in length, between about 12 to about 25 amino acids in length, or about 8, 9, 10, 11, 12, 13, 14, 15, 16, 17, 18, 19, 20, 21, 22, 23, 24, or 25 amino acids in length. Typically, the peptide should not exceed a length which would allow the formation of a tertiary structure, such as, for example, greater than 25 amino acids if present as an isolated molecule. In some cases, the peptide may exceed 25 amino acids. In particular embodiments, the peptide is up to about 8, 9, 10, 11, or 12 amino acids in length.

The isolated peptide may be a mimotope of an epitope of an invertebrate tropomyosin protein. Non-limiting examples of an invertebrate tropomyosin protein includes those found in, e.g., shrimp (Met e 1 and Pen a 1), lobster (Pan s 1 and Hom a 1), crab (Cha f 1), squid (Tod p 1), snail (Tur c 1), oyster (Cra g 1), house dust mites (Der f 10 and Der p 10) and cockroaches (Per a 7 and Bla g 7). In some embodiments, the peptide is a mimotope of an epitope of the tropomyosin protein Met e 1 from *Metapenaeus ensis*.

The peptide when used for immunotherapy can induce antibodies, including blocking antibodies, against a tropomyosin allergen, including one or more tropomyosin proteins or epitopes. In some cases, the peptide can induce the production of antibodies that recognize one or more tropomyosin proteins or one or more tropomyosin epitopes. For example, a peptide provided herein can be used to generate antibodies in a subject that specifically bind to a tropomyosin protein of, for example, shrimp, as well as a tropomyosin protein of, for example, dust mites.

In some embodiments, the peptide includes variants that are further modified to improve their resistance to proteolytic degradation or to optimize solubility properties or to render them more suitable as a therapeutic agent. For example, the peptide further includes analogs containing residues other than naturally occurring L-amino acids, e.g., D-amino acids or non-naturally occurring synthetic amino acids. D-amino acids may be substituted for some or all of the amino acid residues.

In certain embodiments, the peptide comprises naturally-occurring amino acids and/or unnatural amino acids. Examples of unnatural amino acids include, but are not limited to, D-amino acids, ornithine, diaminobutyric acid ornithine, norleucine ornithine, pyriylalanine, thienylalanine, naphthylalanine, phenylglycine, alpha and alpha-disubstituted amino acids, N-alkyl amino acids, lactic acid, halide derivatives of naturally-occurring amino acids (e.g., trifluorotyrosine, p-Cl-phenylalanine, p-Br-phenylalanine, p-I-phenylalanine, etc.), L-allyl-glycine, b-alanine, L-a-amino butyric acid, L-g-amino butyric acid, L-a-amino isobutyric acid, L-e-amino caproic acid, 7-amino heptanoic acid, L methionine sulfone, L-norleucine, L-norvaline, p-nitro-L-phenylalanine, L-hydroxyproline, L-thioproline, methyl derivatives of phenylalanine (e.g., 1-methyl-Phe, pentamethyl-Phe, L-Phe (4-amino), L-Tyr (methyl), L-Phe (4-isopropyl), L-Tic (1,2,3,4-tetrahydroisoquinoline-3-carboxyl acid), L-diaminopropionic acid, L-Phe (4-benzyl), etc.). The peptide may be further modified. For example, one or more amide bonds may be replaced by ester or alkyl backbone bonds. There may be N- or C-alkyl substituents, side-chain modifications, or constraints such as disulfide bridges or side-chain amide or ester linkages.

In some embodiments, the peptide includes both modified peptides and synthetic peptide analogues. Peptides may be modified to improve formulation and storage properties, or to protect labile peptide bonds by incorporating non-peptidic structures.

The peptides of the present invention can be produced by any suitable means known or later discovered in the field, e.g., synthesized in vitro, purified or substantially purified from a natural source, recombinantly produced from eukaryotic or prokaryotic cells, etc.

The peptides may be prepared by in vitro synthesis, using conventional methods as known in the art. For example, peptides may be produced by chemical synthesis, e.g., using solid phase techniques and/or automated peptide synthesizers. In certain instances, peptides may be synthesized using solid phase strategies on an automated multiple peptide synthesizer (Abimed AMS 422) using 9-fluorenylmethyl-oxycarbonyl (Fmoc) chemistry. The peptides can then be purified by reversed phase-HPLC and lyophilized. By using synthesizers, naturally-occurring amino acids may be substituted with unnatural amino acids. The particular sequence and the manner of preparation will be determined by convenience, economics, purity required, and the like. The peptides may alternatively be prepared by cleavage of a longer peptide or full-length protein sequence.

The peptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. Methods which are well known to those skilled in the art can be used to construct expression vectors containing coding sequences and appropriate transcriptional/translational control signals. These methods include, for example, in vitro recombinant DNA techniques, synthetic techniques, and in vivo recombination/genetic recombination. Alternatively, RNA capable of encoding the peptides of interest may be chemically synthesized. One of skill in the art can readily utilize well-known codon usage tables and synthetic methods to provide a suitable coding sequence for any of the peptides of the invention. See, e.g., Sambrook and Russell, Molecular Cloning: A Laboratory Manual, 3rd Ed., 2001, Cold Spring Harbor Laboratory Press; and Ausubel, et al., Current Protocols in Molecular Biology, 1987-2009, John Wiley Interscience.

In some embodiments, the peptide mimotope is conjugated to a carrier protein or adjuvant. A number of carriers are known for this purpose, including various protein-based carriers such as albumin (e.g., bovine serum albumin (BSA)), keyhole limpet hemocyanin (KLH), ovalbumin (OVA), tetanus toxoid (TT), hepatitis B core antigen (HBcAg), high-molecular weight proteins (HMP) from non-typeable *Haemophilus influenzae*, diphtheria toxoid, or bacterial outer membrane protein, all of which may be obtained from biochemical or pharmaceutical supply companies or prepared by standard methodology).

The term "adjuvant" refers to a compound or mixture that enhances the immune response to an antigen. An adjuvant can serve as a depot that slowly releases the antigen and also as a lymphoid system activator that non-specifically enhances the immune response (Hood et al., Immunology, Second Ed., 1984, Benjamin/Cummings: Menlo Park, Calif., p. 384) Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, dinitrophenol, and potentially useful human adjuvants such as BCG (bacille Calmette-Guerin) and *Corynebacterium parvum*. Typically, the adjuvant is pharmaceutically acceptable. In some instances, the adjuvant or carrier can be a serum albumin.

B. Isolated Nucleic Acids

The present disclosure provides an isolated nucleic acid that encodes an isolated peptide described above. In some embodiments, provided herein is an isolated nucleic acid that encodes an isolated peptide having at least about 80%, e.g., at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99%, sequence identity to any one of the sequences set forth in SEQ ID NOS: 1-25 or Table 2. In some embodiments, the isolated nucleic acid provided herein encodes an isolated peptide having 100% sequence identity to any one of sequences set forth in SEQ ID NOS: 1-25 or Table 2. The nucleic acid may encode a peptide comprising at least 8, 9, 10, 11, or 12 contiguous amino acids of any one of the sequences set forth in SEQ ID NOS: 1-25 or Table 2. Additionally, the nucleic acid may encode a peptide comprising an amino acid sequence of any one of SEQ ID NOS: 1-25 or Table 2.

In some embodiments, the nucleic acid encodes a peptide that is not SEQ ID NO: 7 or SEQ ID NO:12. In some instances, the peptide is from about 8, about 9, about 10, about 11, about 12, about 13, about 14, about 15, about 16, about 17, about 18, about 19, about 20, about 21, about 22, about 23, about 24 or about 25 amino acids in length. In some instances, the peptide is from about 8, about 9, about 10, about 11, or about 12 amino acids in length. In some embodiments, the nucleic acid encodes a peptide comprising an amino acid sequence consisting of any one sequence set forth in SEQ ID NOS: 1-25 or Table 2.

The disclosure also provides a vector comprising an isolated nucleic acid provided herein, a host cell comprising a vector, and a peptide encoded by a nucleic acid. The vectors can include the peptide-encoding nucleic acid operably linked to suitable transcriptional and/or translational regulatory elements (e.g., a sequence to control expression) to effect expression in a suitable host cell. The regulatory elements may be derived from mammalian, microbial, viral or insect genes, and include, for example, promoters, enhancers, transcription and translation initiation sequences, termination sequences, origins of replication, and sequences encoding leader and transport sequences. Suitable regulatory elements are selected for optimal expression in a desired host cell. Useful expression vectors can be constructed by methods known to one of ordinary skill in the art, and are also commercially available. Exemplary recombinant viral vectors, include retrovirus, parvovirus, densovirus and baculovirus vectors.

The vector can include a strong constitutive or inducible promoter operatively linked to a nucleic acid of the disclosure. Suitable promoters are well known and readily available to one of ordinary skill in the art and include, for example, bacterial, yeast, viral, mammalian, and insect promoters. Exemplary expression vectors are vectors compatible with mammalian cells.

The host cell can include a vector or an isolated nucleic acid as described herein. The host cell may be prokaryotic or eukaryotic, including bacterial, yeast, insect or mammalian cells. In some cases, the host cell can be a plant cell. In some embodiments, the host cells are plant, insect or mammalian cells. The isolated nucleic acids or vectors, e.g., expression vectors, may be introduced into the host cells by methods known to one of ordinary skill in the art, including transformation, transfection and infection. For example, transfection may be accomplished by any known method, such as liposome-mediated transfection, calcium phosphate-mediated transfection, naked DNA transfection, microinjection or electroporation. Transformation methods suitable for prokaryotic cells are described, for example, in Cohen et al., Proc. Natl. Acad. Sci. (USA) 69:2110 (1972). Transformation of eukaryotic host cells is described, for example, in Sambrook et al., Molecular Cloning: A Laboratory Manual, 3rd edition, Cold Spring Harbor Press, Cold Spring Harbor, N.Y. (2000). The host cells containing the isolated nucleic acid or vectors are useful for replicating the vector and expressing the nucleic acid encoding the peptide of interest, or for replicating and expressing the isolated nucleic acid.

C. Pharmaceutical Compositions

The peptide or nucleic acid encoding the peptide described herein can be formulated for immunotherapy. In some embodiments, the composition includes any one of the isolated peptides described herein. In other embodiments, the compositions include two or more of any of the peptides provided herein. For example, the composition may include 1, 2, 3, 4, 5, 6, 7, 8, 9, 10, 11, 12, 13, 14, 15, 16, 17, 18, 19, 20, 21, 22, 23, 24, or 25 different peptides as set forth in SEQ ID NOS: 1-25. In some embodiments, the composition includes any one of the isolated nucleic acids described herein. In other embodiments, the compositions include two or more of any of the nucleic acids provided herein. For example, the composition may include nucleic acids encoding 1, 2, 3, 4, 5, 6, 7, 8, 9, 10, 11, 12, 13, 14, 15, 16, 17, 18, 19, 20, 21, 22, 23, 24, or 25 different peptides as set forth in SEQ ID NOS: 1-25.

Useful methods for formulating peptides for immunotherapy are known to those of ordinary skill in the art. For example, U.S. Patent Publication No. 2003/0049237 discloses methods of encapsulating antigens to reduce association of antigen with antigen-specific IgE antibodies, thereby reducing the risk of allergic reaction and, possibly, anaphylactic shock. It also discloses methods of modifying IgE binding sites of allergens to reduce allergenicity, for example by masking the IgE binding site or altering an amino acid within the protein. International Patent Publication No. WO 00/74716 A2 discloses various carriers for peptides, as well as peptide-based vaccines in the absence of protein carriers, and compositions comprising a plurality of allergy peptides linked by an inert carrier.

The formulation of pharmaceutical compositions is generally known in the art (see, e.g., *REMINGTON'S PHARMACEUTICAL SCIENCES,* 18TH ED., Mack Publishing Co., Easton, Pa. (1990)) Formulations for use in accordance with the disclosure must be stable under the conditions of manufacture and storage and must also be preserved against the contaminating action of microorganisms such as bacteria and fungi. Prevention against microorganism contamination can be achieved through the addition of one or more of various antibacterial and antifungal agents.

The pharmaceutical forms suitable for administration include sterile aqueous solutions or dispersions and sterile powders for the extemporaneous preparation of sterile injectable solutions or dispersions. In all cases, the form must be sterile and must be fluid to the extent that suitable syringability exists. Typical carriers include a solvent or dispersion medium containing, for example, water-buffered aqueous solutions (i.e., biocompatible buffers), ethanol, polyols such as glycerol, propylene glycol, polyethylene glycol, suitable mixtures thereof, surfactants, or vegetable oils.

Sterilization can be accomplished by an art-recognized technique, including but not limited to filtration or addition of antibacterial or antifungal agents, for example, paraben, chlorobutanol, phenol, sorbic acid or thimerosal. Further, isotonic agents such as sugars or sodium chloride may be incorporated in the subject compositions.

Production of sterile injectable solutions containing a peptide(s), nucleic acid(s) and/or composition(s) is accomplished by incorporating the compound(s) in the required amount(s) in the appropriate solvent with various ingredients enumerated above, as required, followed by sterilization, preferably filter sterilization. To obtain a sterile powder, the above sterile solutions are vacuum-dried or freeze-dried as necessary.

In some embodiments, the peptide(s), nucleic acid(s) and/or composition(s) provided herein are formulated for administration, e.g., oral, nasal, topical, or parental administration in unit dosage form for ease of administration and uniformity of dosage. Unit dosage forms, as used herein, refers to physically discrete units suited as unitary dosages for the subjects, e.g., humans or other mammals to be treated, each unit containing a predetermined quantity of active material calculated to produce the desired therapeutic effect in association with the required pharmaceutical carrier. In some instances, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the peptide(s), nucleic acid(s) and/or composition(s).

Methods for preparing such dosage forms are known to those skilled in the art (see, e.g., *REMINGTON'S PHARMACEUTICAL SCIENCES*, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *REMINGTON'S PHARMACEUTICAL SCIENCES*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

In some embodiments, the composition for administration may be an oral delivery vehicle such as a capsule, cachet or tablet, each of which contains a predetermined amount of the tropomyosin peptide mimic to provide the correct incremental dose to the patient. Oral delivery vehicles may be useful, for example, in avoiding contact between the peptide and the mouth and upper gastrointestinal tract. For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with a peptide(s), nucleic acid(s) and/or composition(s) described herein, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

In some embodiments, a suitable carrier masks the composition, e.g., the peptide or nucleic acid from the mouth and upper gastrointestinal (GI) tract and reduce or prevent local itching/swelling reactions in these regions during administration. For example, a carrier may contain one or more lipid, polysaccharide or protein constituents. In some cases, the carrier is a food product.

For topical administration, the therapeutically effective dose can be in the form of emulsions, lotions, gels, foams, creams, jellies, solutions, suspensions, ointments, and transdermal patches. For administration by inhalation, a peptide(s), nucleic acid(s) and/or composition(s) described herein can be delivered as a dry powder or in liquid form via a nebulizer. Aerosol formulations can be placed into pressurized acceptable propellants such as dichlorodifluoromethane. For parenteral administration, the therapeutically effective dose can be in the form of sterile injectable solutions and sterile packaged powders. Preferably, injectable solutions are formulated at a pH of from about 4.5 to about 7.5

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, the therapeutically effective dose may further comprise other components, for example, anti-allergy drugs, such as antihistamines, steroids, bronchodilators, leukotriene stabilizers and mast cell stabilizers. Suitable anti-allergy drugs are well known in the art. This may be useful in reducing allergic inflammation and increasing tolerance of a tropomyosin allergen.

D. Methods of Administration

In the methods of administration as described herein, the peptides, nucleic acids, or compositions may be administered in a manner compatible with the dosage formulation, in such amount as will be therapeutically effective, and in any way that is medically acceptable for the treatment of the specific allergy. Possible administration routes include oral, nasal, transdermal, topical, and parenteral administration such as intravascular, intravenous, intra-arterial, epicutaneous, subcutaneous, intramuscular, intradermal, intraperitoneal, intraventricular or intraepidural. Examples of oral administration include buccal, sublabial, and sublingual administration. In some cases, administration is by inhalation. In some cases, sustained release administration is also used.

The peptides, nucleic acids, or compositions provided herein can be used to generate antibodies in, for example, a subject with an allergy to shellfish or an arthropod. The method for treating an allergy to shellfish or an arthropod in a subject in need thereof include administering an effective amount of one or more peptides, one or more nucleic acids, and/or one or more compositions described herein. A therapeutically effective amount of the peptide(s), nucleic acid(s) and/or composition(s) represents an amount effective to achieve hyposensitization to a specific allergen. The precise therapeutically effective amount of the peptide(s), nucleic acid(s) and/or composition(s) can be determined by the ordinary skilled artisan with consideration of individual differences in age, weight, extent of disease and condition of the patient.

E. Methods of Nucleic Acid Delivery

In certain aspects, the present invention provides methods for inducing antibodies against an invertebrate tropomyosin protein, e.g., tropomyosin allergen, in a subject by administering a therapeutically effective amount of a nucleic acid encoding one or more peptide mimotopes as described herein. In other aspects, the present invention provides methods for preventing, alleviating or modulating hypersensitivity (an allergic response) to an invertebrate tropomyosin protein, e.g., tropomyosin allergen, in a subject by administering a therapeutically effective amount of a nucleic acid encoding one or more peptide mimotopes as described herein. In yet other aspects, the present invention provides methods for developing or inducing tolerance or desensitization to an invertebrate tropomyosin protein e.g., tropomyosin allergen, in a subject by administering a therapeutically effective amount of a nucleic acid encoding one or more peptide mimotopes as described herein.

As described above, the nucleic acid can be incorporated into a vector such as a bacterial or viral vector. In some instances, the vector is a viral vector system wherein the nucleic acid is incorporated into a viral genome that is capable of transfecting a target cell. In particular embodiments, the nucleic acid can be operably linked to expression and control sequences that can direct expression of the peptide mimotope in the desired target host cells. Thus, the expression of the nucleic acid under appropriate conditions can be achieved in the target cell.

Viral vector systems useful in the expression of the nucleic acid include, but are not limited to, naturally-occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the nucleic acid of interest is inserted into such vectors to allow packaging of the construct, typically with accompanying viral DNA, followed by infection of a sensitive host cell and expression of the nucleic acid of interest.

As used herein, the term "gene delivery system" refers to any means for the delivery of a nucleic acid to a target cell.

In some embodiments, nucleic acids are conjugated to a cell receptor ligand for facilitated uptake (e.g., invagination of coated pits and internalization of the endosome) through an appropriate linking moiety, such as a DNA linking moiety (see, e.g., Wu et al., *J. Biol. Chem.*, 263:14621-14624 (1988); PCT Publication No. WO 92/06180). For example, nucleic acids can be linked through a polylysine moiety to asialo-oromucocid, which is a ligand for the asialoglycoprotein receptor of hepatocytes.

Similarly, viral envelopes used for packaging gene constructs that include the nucleic acid can be modified by the addition of receptor ligands or antibodies specific for a receptor to permit receptor-mediated endocytosis into specific cells (see, e.g., PCT Publication Nos. WO 93/20221, WO 93/14188, and WO 94/06923). In some embodiments, the DNA constructs are linked to viral proteins, such as adenovirus particles, to facilitate endocytosis (Curiel et al., *Proc. Natl. Acad. Sci. U.S.A.*, 88:8850-8854 (1991)).

Retroviral vectors are also useful for introducing the nucleic acid into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild-type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.*, 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis-acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent No. 0178220; U.S. Pat. No. 4,405,712; Gilboa, *Biotechniques*, 4:504-512 (1986); Mann et al., *Cell*, 33:153-159 (1983); Cone and Mulligan, *Proc. Natl. Acad. Sci. USA*, 81:6349-6353 (1984); Eglitis et al., *Biotechniques* 6:608-614 (1988); Miller et al., *Biotechniques*, 7:981-990 (1989); and PCT Publication No. WO 92/07943.

The retroviral vector particles are prepared by recombinantly inserting the desired nucleotide sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the individual is capable of producing, for example, a peptide of interest.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available. Examples of these cell lines include Crip, GPE86, PA317 and PG13 (see Miller et al., *J. Virol.*, 65:2220-2224 (1991)). Examples of other packaging cell lines are described in Cone and Mulligan. *Proc. Natl. Acad. Sci. USA*, 81:6349-6353 (1984); Danos and Mulligan. *Proc. Natl. Acad. Sci. USA*, 85:6460-6464 (1988); Eglitis et al. (1988), supra; and Miller (1989), supra.

Packaging cell lines capable of producing retroviral vector particles with chimeric envelope proteins may be used. Alternatively, amphotropic or xenotropic envelope proteins, such as those produced by PA317 and GPX packaging cell lines may be used to package the retroviral vectors.

F. Kits

Disclosed herein are kits for allergen-specific immunotherapy for tropomyosin allergens. The kits are useful for inducing in a subject (e.g., human subject or other mammal) antibodies against a tropomyosin protein from shellfish or an arthropod, as well as, for developing tolerance in a subject to a tropomyosin protein from shellfish or an arthropod. The kits can also be used for preventing, alleviating or modulating hypersensitivity (allergy) to shellfish and/or an arthropod in a subject (e.g., human subject or other mammal).

In certain aspects, the present invention provides kits comprising a peptide described herein including any one of the peptides set forth in SEQ ID NOS:1-25 or Table 2. In some embodiments, the kit includes two or more, e.g., 2, 3, 4, 5, 6, 7, 8, 9, 10, 11, 12, 13, 14, 15, 16, 17, 18, 19, 20, 21, 22, 23, 24 or 25 different peptides set forth in SEQ ID NOS:1-25 or Table 2. The kit can optionally include an instruction manual describing the use of the contents of the kit.

In some aspects, the present invention provides kits comprising a nucleic acid comprising a nucleotide sequence encoding a peptide described herein including any one of the peptides set forth in SEQ ID NOS:1-25 or Table 2. In some embodiments, the kit includes 1 or more, e.g., 1, 2, 3, 4, 5, 6, 7, 8, 9, 10, 11, 12, 13, 14, 15, 16, 17, 18, 19, 20, 21, 22, 23, 24 or 25 nucleic acids comprising nucleotide sequences encoding 2 or more, e.g., 2, 3, 4, 5, 6, 7, 8, 9, 10, 11, 12, 13, 14, 15, 16, 17, 18, 19, 20, 21, 22, 23, 24 or 25 different peptides set forth in SEQ ID NOS:1-25 or Table 2. In some cases, one nucleic acid of interest can include more than one nucleotide sequence such that each nucleotide sequence encodes a different peptide as set forth in SEQ ID NOS:

1-25. The kit can optionally include an instruction manual describing the use of the contents of the kit.

IV. Examples

The following examples are offered to illustrate, but not to limit, the claimed invention.

Example 1. Screening and Identification of Mimotopes of the Major Shrimp Allergen Tropomyosin Using One Bead One Compound Peptide Libraries The one bead one compound combinatorial (OBOC) peptide library is a powerful tool to identify interactions between specific ligands and receptors. Herein, we applied the OBOC library technology to identify mimotopes of the major shellfish allergen tropomyosin. Mimotopes could be valuable candidates for allergen-specific immunotherapy. The objective of the present study was to identify mimotopes specific to the IgE epitopes of tropomyosin using OBOC peptide libraries. OBOC peptide libraries with 8-12 amino acid residues were screened with serum samples from patients with shellfish allergy for IgE mimotopes of shellfish tropomyosin. Epitope mapping by Episearch of the aligned mimotopes was performed to characterize and confirm the validity of mimotopes. BALB/c mice were immunized with mimotopes conjugated to keyhole limpet hemocyanin (KLH) and assayed for their capacity to induce tropomyosin-specific antibodies. Twenty-five mimotopes were identified from screening five OBOC libraries of 8-12 amino acids in length. Six of the mimotope clusters were mapped to tropomyosin and five of them overlapped with the previously reported epitopes of tropomyosin. One representative mimotope from each of the six clusters was chosen for immunization of BALB/c mice and all the six mimotopes induced tropomyosin-specific $IgG_1$. In conclusion, we demonstrated the successful application of the OBOC library and whole sera to screen and identify multiple shrimp allergen mimotopes, and validated their mimicry potential using both in vivo and in silico methods. This study pioneers the use of OBOC library in food allergies and the potential applications of mimotope-based therapeutic design in food allergies.

Introduction

Mimotopes are short peptides resembling epitopes of an antigen and could serve important applications in immunotherapies. First coined in 1986 (Geysen et al., Mol Immunol, 1986, 23, 709-715), they can induce epitope-specific antibodies when coupled to an immunogenic carrier, which are crucial in numerous therapeutic treatments in neutralizing pathogens. Increasing number of studies have demonstrated success of mimotope-based therapy in various diseases (Knittelfelder et al., Expert Opin Biol Ther, 2009; 9, 493-506; Joyce et al., Proc Natl Acad Sci USA, 2008; 105, 15684-15689; Wang et al., Vaccine, 2012; 30, 2125-2130; Peng et al., J Immunol, 2012; 189, 4909-4920; Zhong et al., Virol J, 2011; 8, 542).

Inspired by the unique property of mimotopes to induce epitope-specific antibodies, the capacity of mimotopes to inhibit IgE-allergen binding (Knittelfelder et al., Expert Opin Biol Ther, 2009; 9, 493-506; Scholl et al., Clin Exp Allergy, 2002; 32, 1583-1588; Subbarayal et al., Allergy, 2013; 68, 1377-1386) has been investigated. Due to their monovalent properties, they are safer than natural extracts/recombinant allergens in allergen-specific immunotherapy (SIT) and can prevent anaphylaxis caused by cross-linking of IgE and degranulation of mast cells. Another key advantage of mimotope-based allergy treatments is the absence of T-cell epitopes such that T-cell mediated late-phase anaphylactic reactions, which commonly occur in the course of SIT, are minimized (Wallmann et al., Clin Exp Allergy, 2010; 40, 650-65).

Despite such advantages, studies on mimotopes in allergies are mostly limited to epitope mapping of allergens (Hantusch et al., J Allergy Clin Immunol 2004; 114, 1294-1300; Untersmayr et al., Mol Immunol, 2006; 43, 1454-1461, Pacios et al, Mol Immunol, 2008; 45, 2269-2276; Szalai et al., Mol Immunol, 2008; 45, 1308-1317; Tiwari et al., Int Arch Allergy Immunol, 2012; 157, 323-330; Ganglberger et al., FASEB J, 2000; 14, 2177-2184) and their applications in immunotherapy are lacking. Biopanning with phage-display peptide libraries is the most common platform used in identifying mimotopes, but this process requires highly purified antibodies or, more often, monoclonal antibodies (mAb). Moreover, developing SIT by identifying mimotopes of allergens with multiple IgE binding epitopes could potentially be problematic and laborious, as biopanning with polyclonal antibodies does not always reveal a single consensus sequence or motif (Ellis et al., Parasite Immunol 2012; 34, 285-295). As a result, multiple rounds of biopanning using different mAbs may be required.

To circumvent the limitations of biopanning of phage-display libraries, we applied one bead one compound (OBOC) combinatorial peptide library technology for high throughput screening of mimotopes. OBOC library is a non-biological synthetic library that has gained much success in drug discovery and isolating cancer-specific peptides (Gray and Brown, Chem Rev 2014; 114, 1020-1081; Aina et al., Mol Pharm, 2007; 4, 631-651. A key advantage of the OBOC library over phage-displayed is the power of a quantitative estimation throughout the screening process, thus allowing the use of less stringent screening agent such as whole cells (Cho et al., ACS Comb Sci, 2013; 15, 393-400) in cancer-specific peptides or whole serum (Raveendra et al., Chem Biol, 2013; 20, 351-359). Herein, we have identified mimotope sequences that are specific to dominant IgE epitopes of the major shellfish allergen tropomyosin from the shrimp Metapenaeus ensis (Met e 1). Our group was the first to clone and identify Met e 1 as the major shrimp allergen (Leung et al., J Allergy Clin Immunol, 1994; 94, 882-890), and recently defined the IgE binding epitopes using in vitro and in silico methods[22]. Since it contains well-characterized multiple immunodominant regions, tropomyosin is an ideal allergen to investigate the potential for applying OBOC library in isolating allergen-associated peptides, i.e., mimotopes.

Methods

Human Serum

Serum samples from adult and adolescent patients with documented clinical shrimp hypersensitivity (n=10; Table 1) were used for screening the OBOC combinatorial peptide libraries. The presence of Met e 1-specific IgE were confirmed by immunoblotting and enzyme-linked immunosorbent assay (Raveendra et al., Chem Biol, 2013, 20:351-359). This study was approved by the Joint Chinese University of Hong Kong (CUHK)—New Territories East Cluster Clinical Research Ethics Committee.

TABLE 1

Clinical characteristics of the patients included in this study. Screening of the OBOC library was performed using pooled serum of patients 1-5 (adolescent/teen pool) or patients 6-10 (adult pool).

| Patient | Age | Sex | Clinical Diagnosis |
| --- | --- | --- | --- |
| 1 | 19 | M | Eczema |
| 2 | 11 | M | Angioedema/Asthma/Eczema |
| 3 | 11 | F | Angioedema/Asthma/Eczema |
| 4 | 14 | F | Anaphylaxis/Eczema |
| 5 | 4 | M | Anaphylaxis/Eczema |
| 6 | 39 | F | Angioedema/Eczema |
| 7 | 54 | F | Angioedema/Eczema |
| 8 | 42 | F | Angioedema/Eczema |
| 9 | 29 | F | Angioedema/Eczema |
| 10 | 43 | M | Angioedema/Eczema |

Synthesis and Screening of OBOC Combinatorial Peptide Library

Figure 5A:
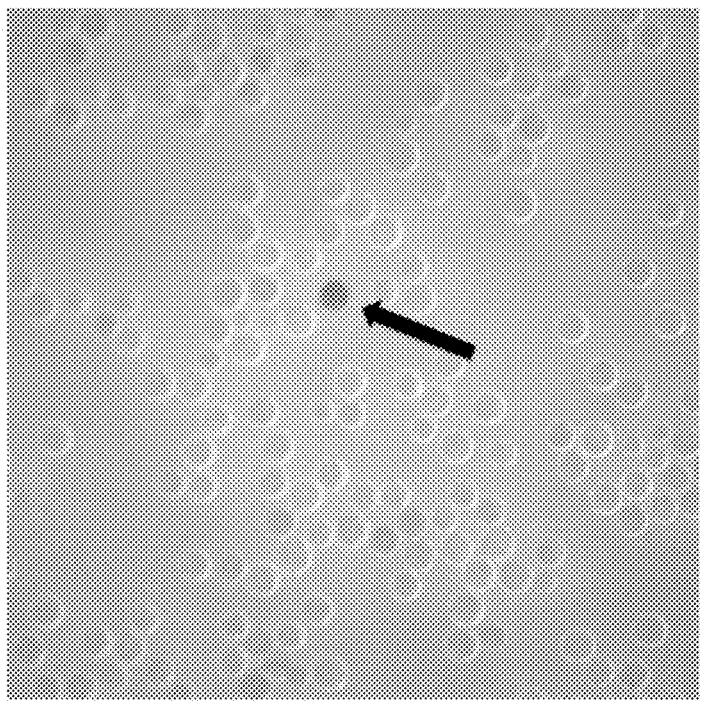
FIGS. 5A and 5B depict beads plated out on a petri dish under a dissection microscope.
Figure 5B:
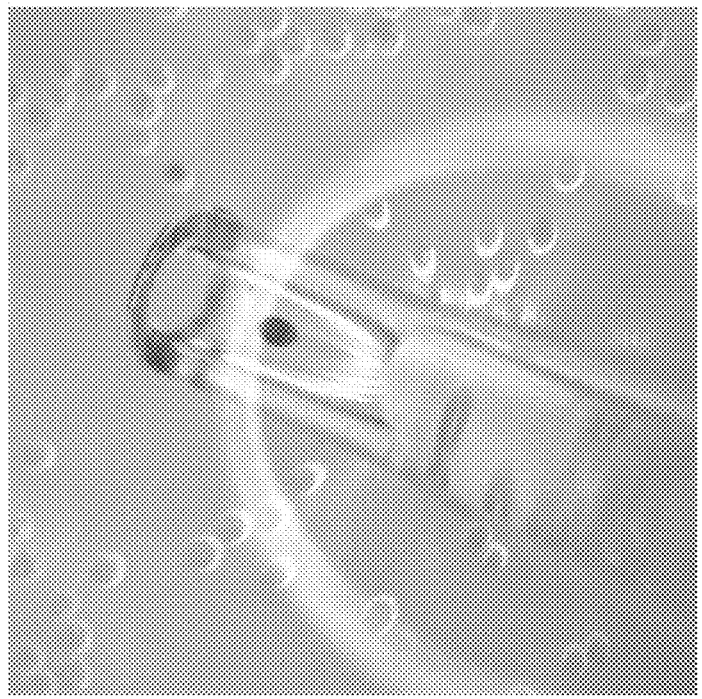

The one-bead-one-compound combinatorial peptide libraries were prepared as described (Lam et al., *Methods*, 1996; 9, 482-493). Briefly, the peptides were synthesized on TentaGel S beads (Rapp Polymere, Germany) by solid-phase synthesis using Fmoc as the protecting group. The split- and mix-method (Lam et al., *Nature*, 1991; 354, 82-84) was adopted using all 19 amino acids except cysteine to avoid inter- or intra-molecular cross-linking. The Fmoc-protected amino acids were anchored to the beads followed by washing with dimethylformamide (DMF) and 20% piperidine (in DMF) for Fmoc deprotection. After the last coupling step, the Fmoc group was removed with 20% piperidine, and the side-chain protecting groups were removed with reagent K (TFA:phenol:water:thiophenol:ethanedithiol, 82:5:5:5:2.5, v/w/v/w/v). Five combinatorial peptide libraries with 8-12 amino acid residues were constructed and screened in this study using a modified two-stage subtraction screening approach (Miyamoto et al., *Anal Biochem*, 2008; 374, 112-120). For each round of screening, 80 μl of the library (approximately 60,000 beads) were used and the incubation process was carried out in a polypropylene disposable column (Qiagen). In the first stage, the beads were blocked with 3% BSA/PBS solution in a revolving mixer at 4° C. overnight. Thereafter, the beads were washed with 0.05% tween/PBS (PBST) and incubated with alkaline phosphatase (AP)-conjugated anti-human IgE (Southern Biotech) at 1:20000 dilution for 1 h at room temperature. The beads were then incubated with 5-bromo-4-chloro-3-indolyl phosphate (BCIP) substrate (Roche) for 30 min at room temperature. The reaction was stopped by incubating with 100 μl 0.1M HCl for 5 minutes. All beads were plated out onto a petri dish and those that turned into a blue color (false positives) were removed with a pipette under a dissecting microscope (FIG. 5A). The rest of the beads were washed and the same procedure as the first stage was repeated but with incubation in pooled human serum (1:20 dilution) for 1 h at room temperature. True positive beads were decolorized by dimethyl formamide (DMF), and both stages were repeated with antibodies of lower dilution (1:50-1:100) and shorter incubation time (30-45 min) to identify beads with the highest affinity to antibody. Only one or two beads with the deepest color were selected from each round of screening. Amino acid sequences of the peptides on the beads were determined via Edman sequencing as described (Lee et al., *Anal Chem*, 2010; 82, 672-679).

Multiple Sequence Alignment

Mimotope sequences were aligned using Clustal Omega (Sievers et al., *Mol Syst Biol*, 2011; 7, 539). Mimotopes that shared at least three amino acids at the same position were clustered as a group. All mimotope sequences were compared to the peptide sequences in MimoDB 2.0 (Huang et al., *Nucleic Acids Res* 2012; 40, D271-277.), an information portal to biopanning results of random libraries, in order to exclude any target-unrelated peptide sequences.

Immunization of BALB/c Mice with Mimotope KLH Conjugates

One mimotope peptide was chosen from each of clusters 1-6 (Table 3) and commercially synthesized (Genscript). The mimotopes were conjugated to keyhole limpet hemocyanin (KLH) using Imject EDC mcKLH Spin Kit (Thermo Scientific) according to manufacturer's instructions. Female BALB/c mice (n=4; 5-6 weeks) were immunized subcutaneously with a mimotope conjugate (50 μg in 200 μl PBS) emulsified in Complete Freund's adjuvant on day 0 and Incomplete Freund's adjuvant on days 14 and 21. Blood samples were collected on day 28 from tail vein of the mice. A Der p 1 mimotope (KGIPNTKAP) (Szalai et al., *Mot Immunol*, 2008; 45, 1308-1317) and an IgE epitope of Met e 1 (KEVDRLEDELVNEKEKYKSI; a.a. 251-270) were also included as negative and positive controls, respectively. All animal protocols were approved by the Animal Experimentation Ethics Committee, CUHK, in accordance with the Department of Health (Government of Hong Kong Special Administrative Region, HKSAR) guidelines in Care and Use of Animals. All experiments were performed under licenses granted from the HKSAR Government.

Detection of Mouse Serum Met e 1-Specific $IgG_1$ and $IgG_{2a}$ in ELISA

ELISA was performed as previously described (Wai et al., *PLoS One*, 2014; 9, e111649) to detect Met e 1-specific IgG antibodies. Recombinant Met e 1 (0.5 μg per well/100 μl $NaHCO_3$, pH 9.6 coating buffer) were coated onto MaxiSorp microtitre plates (Nunc) at 37° C. for 3 h, washed with PBST and blocked with 10% FBS (Gibco) for 2 h at room temperature. Serum samples were diluted 1:100 in 10% FBS and incubated overnight at 4° C. After washing, the plates were incubated with biotinylated goat anti-mouse $IgG_1$ or $IgG_{2a}$ (Southern Biotech) at 1:2000 dilution, followed by incubation with Horseradish Peroxidase Avidin D (Vector) for 30 min. Final washes were repeated 5 times with PBST and the plates were incubated with 100 μl/well of TMB substrate reagent set (BD Biosciences). 100 μl of 0.1M sulfuric acid was added to each well to stop the reaction after 10 min of incubation and the optical density at 450 nm was determined using microplate reader (BioRad Model 680). ELISA to determine the $IgG_1$ titers was repeated as described above using pooled serum diluted 1:100, 1:200, 1:400, 1:800 and 1:1600 in 10% FBS.

Homology Modeling

Tropomyosin from *Metapenaeus ensis* (Met e 1) was used as the model allergen in this study. The tropomyosin allergen Pen a 1 from another shrimp species, *Penaeus aztecus* (Niall et al., *Methods Enzymol*, 1973; 27, 942-1010) was also included for comparison as its epitopes are characterized (Ayuso et al., *Int Arch Allergy Immunol*, 2002; 127, 27-37). Pen a 1 and Met e 1 are almost identical in amino acid sequence except a single substitution at position 79. The 3-D structure of Met e 1 was constructed by the Swiss-Model Protein Modeling Server (Arnold et al., *Bioinformatics*, 2006; 22, 195-201) using the wild boar *Sus scrofa* (PDB 1C1G) tropomyosin as modeling template.

Epitope Mapping by EpiSearch

Epitope mapping of Met e 1 was carried out with EpiSearch (Negi et al., *Bioinform Biol Insights* 2009; 3, 71-81) using the clustered mimotopes as data input. The EpiSearch program is an automated tool for predicting the possible location of conformational epitopes on the surface of an antigen, which are then ranked according to frequency distribution of similar residues in the patch of mimotope input. All EpiSearch predictions were based on default conditions (Patch Size=12; Area cutoff=10; Accuracy cutoff=3). Linear or cyclic mimotopes from six irrelevant allergens previously identified were also mapped against Met e 1 as a negative control.

Statistical Analysis

Met e 1-specific IgG$_1$ levels were compared between each group of mice receiving mimotope conjugates and control group receiving KLH alone using t-test (p<0.05) in SigmaStat 3.1.

Results

Library Screening and Multiple Sequence Alignment

From screening the five combinatorial peptide libraries, 25 mimotope sequences were obtained (Table 2). There is no significant difference in the pattern of epitope recognition between adults and children. No sequences were found on MimoDB2.0, confirming their relevance to this allergen but not target-unrelated peptides. 20 of the 25 mimotope sequences could be grouped into seven clusters each with at least three amino acid residues in common at the same position, based on the alignment of Clustal Omega (FIG. 1). Non-clustering mimotopes were not included in subsequent analyses.

TABLE 2

Mimotope sequences obtained through screening OBOC combinatorial library with pooled serum form shellfish allergy patients.

| Mimotope Sequence | SEQ ID NO: | Library | Serum Pool |
|---|---|---|---|
| KRLFERDG | SEQ ID NO: 7 | X8 | Adult |
| LHTIPVMI | SEQ ID NO: 13 | X8 | Adolescent/Children |
| DIHEESPD | SEQ ID NO: 3 | X8 | Adolescent/Children |
| MHVLLMRRD | SEQ ID NO: 18 | X9 | Adult |
| KLAYMHVRV | SEQ ID NO: 17 | X9 | Adult |
| GTKLQHFRQ | SEQ ID NO: 9 | X9 | Adult |
| RIWVGHFML | SEQ ID NO: 1 | X9 | Adult |
| HDGIPDWSM | SEQ ID NO: 4 | X9 | Adult |
| FFEAGKGNK | SEQ ID NO: 24 | X9 | Adult |
| RAVFFRNDH | SEQ ID NO: 25 | X9 | Adult |
| YKTPHQVFQ | SEQ ID NO: 11 | X9 | Adult |
| HWHAKNAQR | SEQ ID NO: 21 | X9 | Adult |
| HWSSTRRFPP | SEQ ID NO: 16 | X10 | Adult |
| RPWPQAHPNL | SEQ ID NO: 20 | X10 | Adult |
| RTIPTMEIWIH | SEQ ID NO: 12 | X10 | Adolescent/Children |
| TFVDDRRFMS | SEQ ID NO: 15 | X10 | Adolescent/Children |
| VTWERTTKHQHW | SEQ ID NO: 10 | X12 | Adult |
| MVGWPPKHRKDK | SEQ ID NO: 19 | X12 | Adult |
| MRIIVIHLNWMYWK | SEQ ID NO: 2 | X12 | Adult |
| WQRHMVHTWRWM | SEQ ID NO: 22 | X12 | Adult |
| TKYERGGRVRKI | SEQ ID NO: 6 | X12 | Adult |
| KGHTKAHHGKNT | SEQ ID NO: 8 | X12 | Adult |
| ASSRWLGKVHDV | SEQ ID NO: 23 | X12 | Adult |
| IKALSRLQTIYG | SEQ ID NO: 14 | X12 | Adult |
| PTDVERKTSYTL | SEQ ID NO: 5 | X12 | Adolescent/Children |

The serum pool used for mimotope screening is indicated on the right.

Induction of Met e 1-Specific IgG$_1$ and IgG$_{2a}$ in BALB/c Mice after Mimotope Immunization By ELISA, all six mimotope conjugates developed increased levels of Met e 1-specific IgG$_1$, compared to the control group receiving KLH alone or the irrelevant mimotope (p<0.05)(FIG. 2A). The capacity to induce Met e 1-specific antibodies was comparable between the mimotopes and the Met e 1 epitope, except for mimotope GTKLQHFRQ (SEQ ID NO: 9) from cluster 4 which exhibited lower capacity (p=0.03). $IgG_{2a}$ levels were not significantly different among groups. Met e 1-specific $IgG_1$ were detected even at dilution 1:800 in mice receiving mimotope immunization. Met e 1-specific $IgG_1$ was still detectable at 1:1600 dilution in sera samples of mice immunized with mimotope DIHEESPD (SEQ ID NO: 3) of cluster 2 (FIG. 2A).

Homology Modeling and the Mapping of Epitopes on Met e 1 by EpiSearch

Figure 3A:
FIGS. 3A-3D provide a homology model of Met e 1 based on *Sus scrofa* tropomyosin sequence for illustrating the location of predicted and identified epitopes.
Figure 3B:
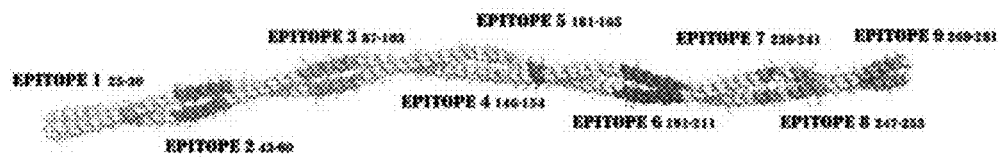
Figure 3C:
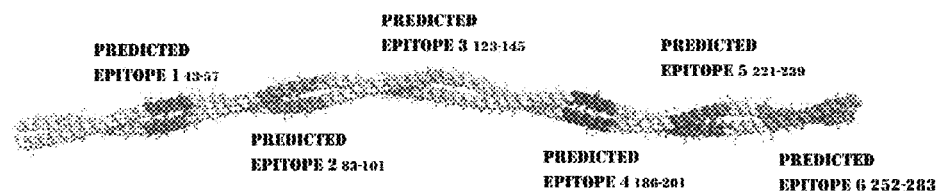

Only the top two predictions produced by EpiSearch with a ranking score >0.800 were included in the analysis (Table 3). Eleven predicted patches were suggested by EpiSearch, with Cluster 6 having only one prediction above the threshold and Cluster 7 having none. After integrating the 11 predicted patches, six epitope regions were identified: Met e $1^{43-57}$, Met e $1^{83-101}$, Met e $1^{123-145}$, Met e $1^{186-201}$, Met e $1^{221-239}$ and Met e $1^{252-283}$ (Table 2, FIG. 3C).

TABLE 3

Epitope mapping of Met e 1 by EpiSearch using mimotopes obtained through screening OBOC combinatorial library with pooled serum form shellfish allergy patients.

| Cluster | Minotope Sequence | Ranking Score | Patch Range |
|---|---|---|---|
| Cluster 1 | | | |
| a) | RIWVGHFML* (SEQ ID NO: 1) MRIMHLNWMYWK (SEQ ID NO: 2) | 0.875 | 43-57 |
| b) | RIWVGHFML (SEQ ID NO: 1) MRIMHLNWMYWK (SEQ ID NO: 2) | 0.800 | 83-95 |
| Cluster 2 | | | |
| a) | DIHEESPD* (SEQ ID NO: 3) HDGIPDWSM (SEQ ID NO: 4) | 1.00 | 269-283 |
| b) | DIHEESPD (SEQ ID NO: 3) HDGIPDWSM (SEQ ID NO: 4) | 0.855 | 131-145 |
| Cluster 3 | | | |
| a) | PTDVERKTSYTL (SEQ ID NO: 5) TKYERGGRVRKI (SEQ ID NO: 6) KRLFERDG* (SEQ ID NO: 7) | 0.933 | 252-267 |
| b) | PTDVERKTSYTL (SEQ ID NO: 5) TKYERGGRVRKI (SEQ ID NO: 6) KRLFERDG (SEQ ID NO: 7) | 0.900 | 186-201 |
| Cluster 4 | | | |
| a) | KGHTKAHHGKNT (SEQ ID NO: 8) GTKLQHFRQ* (SEQ ID NO: 9) | 0.892 | 221-236 |

TABLE 3-continued

Epitope mapping of Met e 1 by EpiSearch using mimotopes obtained through screening OBOC combinatorial library with pooled serum form shellfish allergy patients.

| Cluster | Minotope Sequence | Ranking Score | Patch Range |
|---|---|---|---|
| | VTWERTTKHQHW (SEQ ID NO: 10) YKTPHQVFQ (SEQ ID NO: 11) | | |
| b) | KGHTKAHHGKNT (SEQ ID NO: 8) GTKLQHFRQ (SEQ ID NO: 9) VTWERTTKHQHW (SEQ ID NO: 10) YKTPHQVFQ (SEQ ID NO: 11) | 0.802 | 224-239 |
| Cluster 5 | | | |
| a) | RTIPTMHWIH (SEQ ID NO: 12) LHTIPVMI* (SEQ ID NO: 13) IKALSRLQTIYG (SEQ ID NO: 14) | 0.917 | 224-239 |
| b)** | RTIPTMHWIH (SEQ ID NO: 12) LHTIPVMI (SEQ ID NO: 13) | 0.900 | 88-101 |
| Cluster 6 | TFVDDRRFMS (SEQ ID NO: 15) MHVLLMRRD (SEQ ID NO: 18) HWSSTRRFPP (SEQ ID NO: 16) KLAYMHVRV* (SEQ ID NO: 17) | 0.890 | 123-137 |
| Cluster 7 | MVGWPPKHRKDK (SEQ ID NO: 19) RPWPQAHPNL (SEQ ID NO: 20) | / | / |

*Mimotopes selected for in vivo verification in each cluster.
**The mimotope IKALSRLQTIYG (SEQ ID NO: 14) is solely responsible for mapping to a.a. 224-239. We chose to adopt the prediction without mimotope IKALSRLQTIYG (SEQ ID NO: 14) for cluster 5 which yielded the second highest ranking score.

Only the predictions with the highest (a) and second highest (b) ranking score for each cluster were shown and included in this study. Cluster 6 has only one prediction above the threshold score (ranking score >0.800) and none for cluster 7. A total of 11 patches were predicted from the seven mimotope clusters.

TABLE 4

Analysis of EpiSearch data and comparison between predicted epitopes and reported epitopes.

| Clusters/ Negative control | Predicted Patch | Patch Size | Epitope Coverage[1] (Pen a 1/ Met e 1) | Overlap Ratio[2] (Pen a 1/ Met e 1) | Patch Similarity[3] |
|---|---|---|---|---|---|
| 1a | 43-57 | 15 | 1.00/0.833 | 1.00/1.00 | 0.667 |
| 1b, 5b | 83-101 | 19 | 0.809/0.882 | 0.894/0.789 | 0.579 |
| 2b, 6 | 123-145 | 23 | 0.813/0.00 | 0.565/0.00 | 0.739 |
| 3b | 186-201 | 16 | 0.938/0.285 | 0.938/0.375 | 1.00 |
| 4a, 4b, 5a | 221-239 | 19 | 0.00/0.667 | 0.00/0.211 | 1.00 |

TABLE 4-continued

Analysis of EpiSearch data and comparison between predicted epitopes and reported epitopes.

| Clusters/ Negative control | Predicted Patch | Patch Size | Epitope Coverage[1] (Pen a 1/ Met e 1) | Overlap Ratio[2] (Pen a 1/ Met e 1) | Patch Similarity[3] |
|---|---|---|---|---|---|
| 2a, 3a | 252-283 | 32 | 0.868/0.773 | 1.00/0.531 | 0.75 |
| Bet v 1 | / | / | / | / | / |
| Der p 1 | / | / | / | / | / |
| Der p 2 | 221-236 | 16 | 0.00/0.167 | 0.00/0.063 | 0.938 |
| Bla g 2 | 114-128 | 15 | 0.00/0.00 | 0.00/0.00 | 0.933 |
| Parvalbumin | / | / | / | / | / |
| Pru p 3 | 21-36 | 16 | 0.00/1.00 | 0.00/0.375 | 0.938 |

[1]Overlapping residues/Total no. of residues in reported epitope.
[2]Overlapping residues/Total no. of residues in predicted patch.
[3]Identical residues in mimotopes/Identical Residues in predicted patch.

Comparison Between Mimotope Sequences and Predicted Patch

Figure 4:
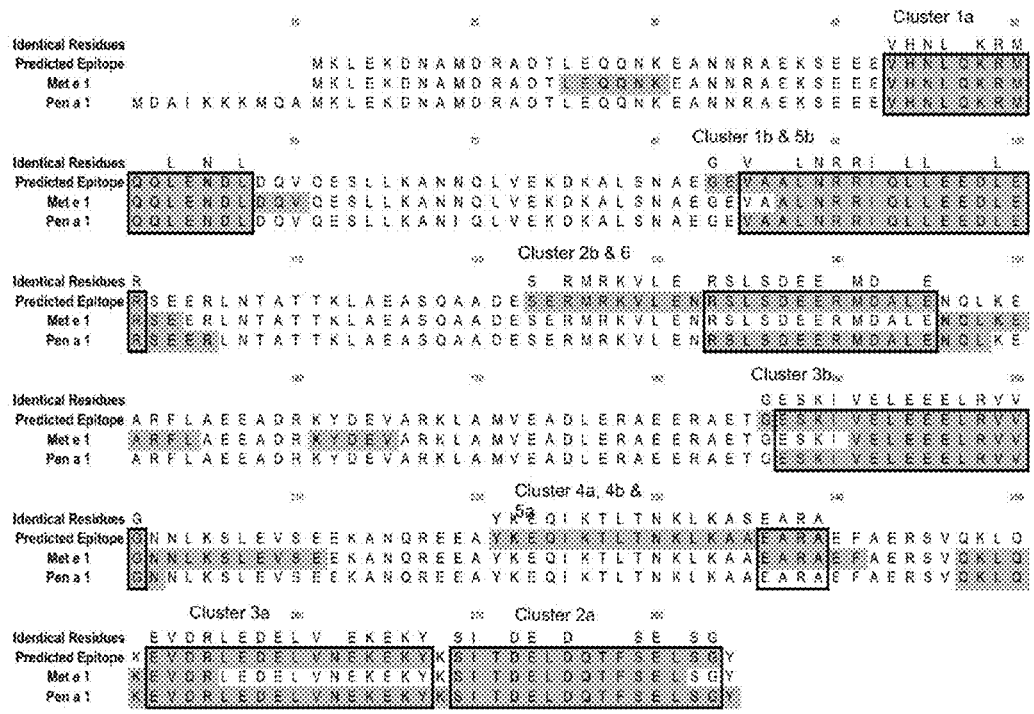
FIG. 4 shows the predicted epitopes (SEQ ID NO: 26) by EpiSearch using mimotopes as sequence inputs compared to the previously identified epitopes. Met e 1 (SEQ ID NO: 27) and Pen a 1 (SEQ ID NO: 28) differs by one amino acid at position 69. Identical residues refer to the consensus residues between the mimotope input and the predicted epitopes. Shaded amino acids represent predicted epitopes or identified epitopes of Met e 1 and Pen a 1. Boxed sequences represent overlapping regions between predicted and identified epitopes.

The patch similarity was calculated by the percentage of identical residues found in the mimotope input relative to the predicted patch (FIG. 4). The amino acid residues of the mimotope sequences are generally more than 50% alike with the predicted patches (0.579-1.00). The amino acid residues in predicted epitope of Met e $1^{186-201}$ and Met e $1^{221-239}$ were all found in the corresponding mimotope input (Table 4).

Comparison Between Predicted and Genuine Epitopes

Figure 3D:

To validate the specificity of the mimotopes, the predicted patches were compared to the previously reported epitopes of Met e 1 and Pen a 1 by determining epitope coverage and overlapping ratio (Table 4). Five of the six predicted epitope regions, Met e $1^{43-57}$ Met e $1^{83-101}$ Met e $1^{123-145}$ Met e $1^{186-201}$, and Met e $1^{252-283}$, overlapped with Pen a 1 epitopes (FIG. 3A)[30] with high epitope coverage (0.809-1.00). Met e $1^{43-57}$ exactly mapped to epitope region 1 from Val43 to Leu57 (epitope coverage=1.00). Two predicted patches Met e $1^{43-57}$ and Met e $1^{252-283}$ were completely within the genuine epitope (overlap ratio=1). Remarkably, the predicted patches covered all five major IgE binding regions of Pen a 1. Met e 1 epitopes (FIG. 3B) (Wai et al., *PLoS One* 2014; 9, e111649) were found to overlap with five of the six predicted regions (Table 4, epitope coverage=0.285-0.882). The predicted epitope Met e $1^{221-239}$ which did not overlap with any of the Pen a 1 epitopes, overlapped with epitope 7 (a.a. 236-241) of Met e 1. Linear or cyclic mimotopes from six irrelevant allergens (Table 5) were also mapped to Met e 1 using EpiSearch (Table 4, FIG. 3D). Only half of the irrelevant inputs matched to Met e 1, and only a prediction based on Pru p 3 overlapped with a short epitope at Met e $1^{25-30}$; none overlapped with Pen a 1 epitopes.

TABLE 5

Mimotopes from irrelevant allergens were included as negative control for epitope mapping by EpiSearch.

| Allergen | Mimotope | SEQ ID NO: | Predicted Patch | Ranking Score | Reference |
|---|---|---|---|---|---|
| Bet v 1 | CQQTLSVRALS | SEQ ID NO: 29 | / | / | Ganglbergel et al. |
| | CGGTPPSLPTC | SEQ ID NO: 30 | | | |
| | CGGTRRPIASC | SEQ ID NO: 31 | | | Szalai et al. |
| Der p 1 | KGIPNTKAP | SEQ ID NO: 32 | / | / | |
| | GIREVWPAG | SEQ ID NO: 33 | | | |
| | KGTTGVRNT | SEQ ID NO: 34 | | | |
| Der p 2 | FVVEYTKKW | SEQ ID NO: 35 | 221-236 | 0.828 | Szalai et al. |
| | SWWNLPQIG | SEQ ID NO: 36 | | | |
| | KGITTKWMA | SEQ ID NO: 37 | | | |
| | AGISYTKTW | SEQ ID NO: 38 | | | |
| Bla g 2 | SMMKADFDEEPR | SEQ ID NO: 39 | 114-128 | 1.00 | Tiwari et al. |
| | SMMKADFEEEPR | SEQ ID NO: 40 | | | |
| Paravalbumin | CYRGVTLAGHRC | SEQ ID NO: 41 | / | / | Untersmayr et al. |
| | CFKGVRLDGTPC | SEQ ID NO: 42 | | | |
| | CYRGARVDGLMC | SEQ ID NO: 43 | | | |
| Pru p 3 | PSRTPRPEWAXL | SEQ ID NO: 44 | 21-36 | 0.875 | Pacios et al. |
| | TSRPALLNDQGH | SEQ ID NO: 45 | | | |

Ganglberger et al., FASEB J 2000; 14, 2177-2184. Szalai et al., Mol Immunol 2008; 45, 1308-1317. Tiwari et al., Int Arch Allergy Immunol 2012; 157, 323-330. Untersmayr et al., Mol Immunol 2006; 43, 1454-1461. Pacios et al., Mol Immunol 2008; 45, 2269-2276

The mimotopes were either screened from linear or a cyclic library and correspond to a single epitope. Only 3 out of 6 of the mimotope clusters could be mapped to Met e 1 with a ranking score >0.800 and only predictions from Pru p 3 overlapped with a genuine epitope on Met e 1.

Discussion

In this study, we have demonstrated the application of OBOC combinatorial library technology to obtain IgE mimotopes of shrimp tropomyosin using whole serum from patients with shellfish allergy. The mimicry potential and specificity of mimotopes were further validated using in vivo and in silico analysis. Mice immunized with mimotope-KLH conjugates exhibited Met e 1-specific $IgG_1$ but not mice receiving irrelevant mimotope or KLH alone. This data suggests that mimotope-specific antibodies are able to recognize at least one or more epitopes on tropomyosin. Met e 1-specific $IgG_1$ levels were detectable at as low of a dilution as 1:800 in mimotope immunized mice, comparable to the positive control groups. This indicates a strong affinity of the mimotope-induced antibodies to the native epitopes, even when the antibodies were raised against a peptide instead of the whole antigen. From a clinical perspective, the data demonstrates the capacity of mimotopes to induce antibodies to their corresponding epitopes, which could be useful in generating blocking antibodies in SIT. Although the antibodies induced by mimotopes are primarily of the $IgG_1$ isotype in this study, their potential to induce $IgG_{2a}$ isotypes with Th1-adjuvant such as monophyphoryl lipid A (Wheeler et al., Int Arch Allergy Immunol, 2001; 126, 135-139) or chitosan (Li et al., Cell Mol Immunol, 2009; 6, 45-50) could be further investigated.

Although mixtapes may not share sequence homology with their corresponding epitopes, the amino acid composition is quite similar between the mimotopes (FIG. 4) and epitopes in our study as indicated by patch similarity (>0.500). This could be due to the relatively simple structure of tropomyosin and a lack of spatial organization of the epitopes. The mimicry of mimotopes is therefore mainly attributed to the similarity in physiochemical properties, i.e., the amino acid composition. For mapping conformational epitopes on the surface of globular proteins with more complex structures, a cyclic peptide library could be applied (Lam et al., Methods, 1996; 9, 482-493).

By mapping the clustered mimotopes onto tropomyosin, we also confirmed the validity of the mimotopes by comparing with the previously identified epitopes of Met e 1 (Wai et al., PLoS One 2014; 9, e111649) and Pen a 1 (Ayuso et al., Int Arch Allergy Immunol 2002; 127, 27-37). All epitopes predicted by EpiSearch were found to overlap completely or partially with at least one of the epitopes of Met e 1 or Pen a 1. The overlap ratios of the predicted clusters and genuine epitopes are higher in Pen a 1 than Met e 1 (Table 2), which might be due to the different mapping methods used for the two allergens. The Pen a 1 epitopes were identified by microarray of overlapping linear peptides spanning the entire length of Pen a 1 while the Met e 1 epitopes were mapped by both in vitro and in silico methods including ELISA, dot immunoblotting and epitope prediction models. The Met e 1 epitopes would therefore be more distinct and refined, thus requiring a larger number of mimotopes to define the epitopes at a higher resolution. Nevertheless, only half of the six irrelevant mimotopes were mapped to Met e 1, with only a single predicted epitope found to overlap with a short epitope of Met e 1 and none with Pen a 1. These results highlight the specificity of the identified mimotopes and the power of EpiSearch as a tool for in silico validation. In fact, compared to a previous study using EpiSearch as an epitope mapping tool with subsequent verification by X-ray co-crystallography of monoclonal antibodies and the predicted epitopes (Tiwari et al., Int Arch Allergy Immunol 2012; 157, 323-330), the EpiSearch predictions in our study have comparable or even higher epitope coverage, overlap ratio and patch similarity, affirming the credibility and relevance of mimotopes selected from OBOC library.

Results from epitope mapping highlight the key advantage of the OBOC library: screening using pooled serum samples with polyclonal antibodies can simultaneously identify six epitopes with different specificities. The biopanning method for phage-displayed libraries usually utilizes the antibody as the capturing agent, and a homogenous population of antibodies is required to obtain a well-defined consensus sequence. Using polyclonal antibodies for biopanning is not feasible, as the sequences identified may correspond to different epitopes. It is also difficult to discern the positive hits against a background of non-binding sequences, as this process is non-quantitative (Gray et al., Bioconjug Chem, 2013; 24, 85-96). Hence, most studies involving biopanning for mimotope screening of allergens requires mAb (Szalai et al., Mol Immunol, 2008; 45, 1308-1317; Tiwari et al., Int Arch Allergy Immunol, 2012; 157, 323-330) or affinity-purified antibodies (Hantusch et al., J Allergy Clin Immunol 2004; 114, 1294-1300; Untersmayr et al., Mol Immunol, 2006; 43, 1454-1461), imposing a major technical limitation.

In contrast to the phage-displayed libraries which are non-quantitative, the OBOC combinatorial library offers a direct assessment of the affinity of individual peptides by the color intensity of beads. Moreover, unlike phage-display libraries where only a few peptides are displayed by each phage, there are up to 100 pmol or $10^{13}$ copies of the same peptide on a single bead in an OBOC library (Lam et al., Methods, 1996; 9, 482-493). The high number of copies ensures higher sensitivity so that a more diluted antibody concentration (10-100 fold lower) can be used to reduce background signals. As such, a negative screening with non-allergic serum to deplete non-specific binding to irrelevant serum IgE is not needed. It is also unnecessary to deplete IgG in the serum samples as the use of a specific anti-IgE secondary antibody would ensure the isotype specificity. By using pooled serum from multiple patients, the tropomyosin-specific IgE level would well exceed the level of irrelevant serum IgE. Moreover, the two-stage screening approach and cross-checking with sequences in MimoDB could further ensure the mimotope sequences are specific to the target allergen.

Screening of the OBOC library is much faster than biopanning with phage-display libraries. The whole screening process can be completed in two days for an OBOC library with 10 million beads compared to six days in biopanning using a standard protocol. Additionally, only standard laboratory equipment is required for the synthesis and screening of OBOC library. The rate-limiting step for library screening is usually peptide sequencing by Edman Degradation, but various methods are available to shorten the time required for peptide sequencing on beads (Lee et al., J Comb Chem, 2008; 10, 807-809; Chen et al., J Comb Chem, 2009; 11, 604-611; Franz et al., J Comb Chem, 2003; 5, 125-137). Moreover, handling and maintenance of chemical libraries such as OBOC is much easier and does not require complex procedures such as phage amplification, phage titering, and strain maintenance. Lastly, major disadvantages of biological libraries—such as phage contamination or inadequate peptide diversity due to biological pressure—are avoided.

As demonstrated by this pioneering study, the identification of multiple IgE mimotopes using whole serum and an OBOC combinatorial library is an attractive alternative to the conventional biopanning of phage-displayed libraries. The OBOC technology could shed light on the overwhelming potential of mimotopes as a valuable target for epitope mapping and designing mimotope-based immunotherapy for allergy. One potential application of the OBOC library is a patient-specific approach that is hard to achieve using phage-displayed libraries. Such patient-specific mimotope screening would have added useful information about specific IgE epitopes, such as the relevance and binding frequency of each IgE epitope. Furthermore, it could lead to a revolutionary approach for SIT by tailoring the most relevant blocking antibodies for each patient based on their own sensitization profile. This patient-specific approach could reduce neo-sensitization and maximize the blocking capacity of antibodies induced, further improving the therapeutic safety and efficacy of SIT.

In conclusion, we have identified and validated mimotopes of tropomyosin obtained by screening OBOC combinatorial peptide libraries. This new approach could overcome the limitations imposed by biopanning of phage-displayed libraries and paves the way for more prominent use of mimotopes to study allergy.

Example 2. Validation of Mimotope Conjugates

This example shows that mice immunized with KLH-mimotope conjugates had elevated tropomyosin antibodies compared to mice immunized to only the carrier protein keyhole limpet-hemocyanin (KLH). In addition, the results show that a higher percentage of IgE were bound to the mimotope conjugate than to the tropomyosin epitope (Met e 1).

Figure 6:
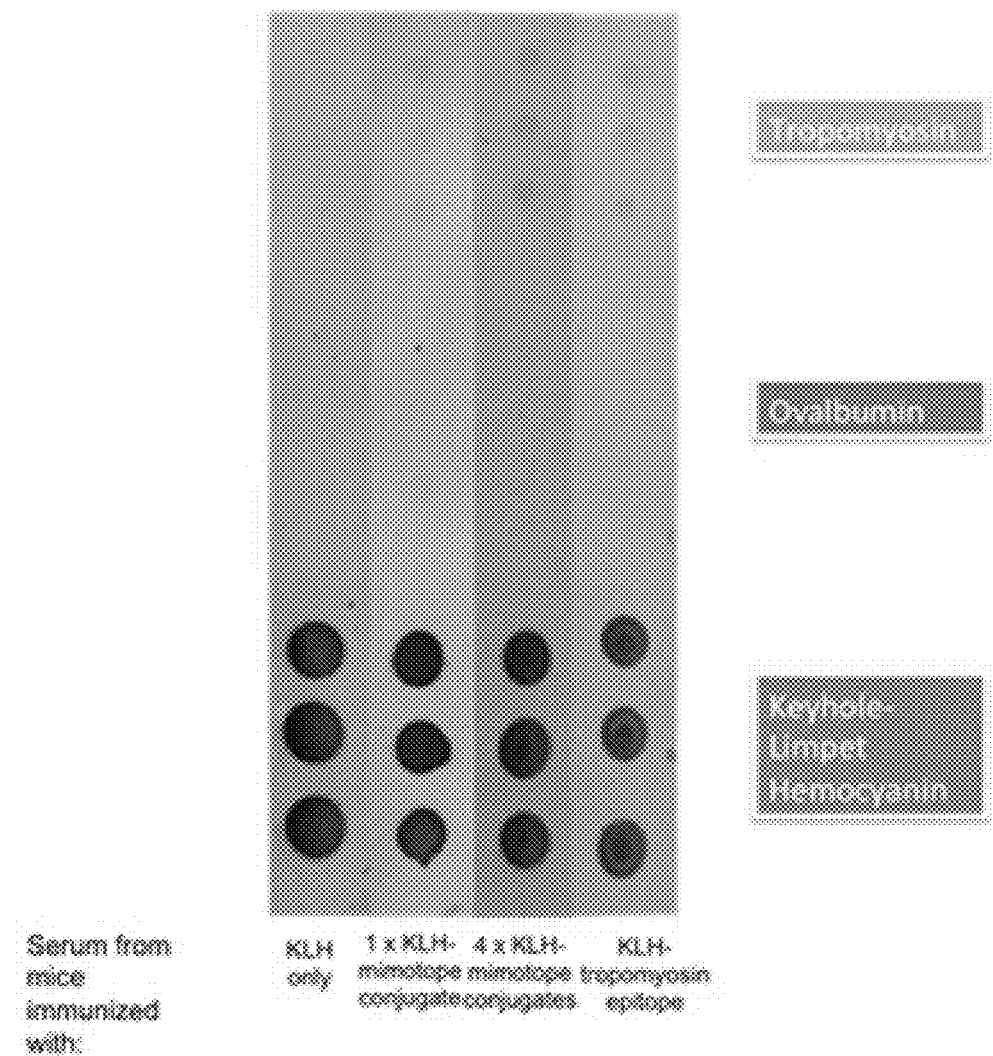
FIG. 6 shows that mimotope-immunized mice are immunoreactive to the mimotope-conjugate. The antiserum from the mimotope-immunized mice contains antibodies that recognize tropomyosin, and not ovalbumin.

The mimotopes described above were conjugated to keyhole limpet hemocyanin (KLH) using Imject EDC mcKLH Spin Kit (Thermo Scientific) according to manufacturer's instructions. The mimotope conjugates that were produced included 1×KLH-mimotope conjugate or 4×KLH mimotope conjugates. Female BALB/c mice (n=4; 5-6 weeks) were immunized subcutaneously with a mimotope conjugate (50 µg in 200 µl PBS) emulsified in Complete Freund's adjuvant on day 0 and Incomplete Freund's adjuvant on days 14 and 21. Blood samples were collected on day 28 from tail vein of the mice. Dot immunoblotting was performed to detect the presence of antibodies to the tropomyosin allergen in the samples. FIG. 6 shows the samples from the mice immunized with either the 1×KLH-mimotope conjugate, the 4×KLH-mimotope conjugates (4 different KLX-mimotope conjugates) or the KLH-tropomyosin epitope conjugate produced antibodies that specifically bind to tropomyosin.

Figure 7:
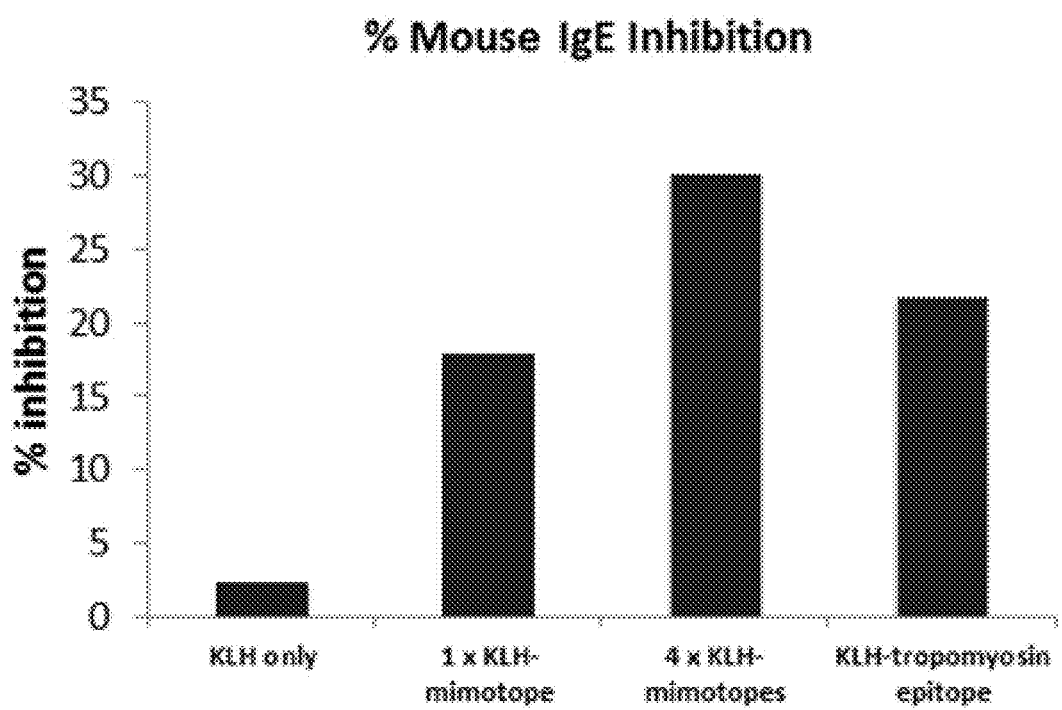
FIG. 7 illustrates the inhibitory potential of IgG antibodies towards the Met e 1 allergen.

A competitive inhibition ELISA was performed to evaluate the blocking capacity mimotope-induced blocking antibodies. The 96-well ELISA plates were coated with 5 µg/ml of the *Metapenaeus* tropomyosin allergen (Met el) in 0.05 M carbonate buffer overnight at 4° C. and blocked with 1% BSA/PBS for 2 h. The plates were washed and incubated with serum samples from mice immunized with the KLH carrier protein alone, the 1×KLH-mimotope conjugate, the 4×KLH-mimotope conjugate or the KLH-tropomyosin epitope conjugate overnight at 4° C. Thereafter, sera from tropomyosin-sensitized mice were added and incubated at room temperature for 2 hours. After washing, plates were incubated with biotinylated anti-mouse IgE antibodies (BD Pharmigen) and HRP-Avidin D. The plates were developed with TMB substrate reagent set (BD Biosciences) and the reaction was terminated by 2N $H_2SO_4$. The blocking ability of the induced IgG antibodies was determined using the equation $[(OD_{no\ inhibitor} - OD_{inhibitor})/OD_{no\ inhibitor}] \times 100$ and expressed as percentage inhibition. The 4×KLH-mimotope conjugate-induced IgG antibodies inhibited IgE of the tropomyosin-sensitized mice from binding to the tropomyosin allergen (Met el) (FIG. 7). The inhibition was greater for the 4×KLH-mimotope conjugate compared to the 1×4×KLH-mimotope conjugate and the KLH-tropomyosin epitope.

It was also determined that mice immunized with more than one mimotope conjugate had a higher antibody titer compared to those immunized with one mimotope conjugate. This is similar to the results from the competitive inhibition ELISA that showed that antiserum from mice receiving 4 different mimotopes inhibited IgE binding better than antiserum from mice immunized with only one mimotope.

Example 3. Therapeutic Effect of Mimotopes in a Mouse Model of Allergy

We have tested the therapeutic effects of mimotopes using an established mouse model of shrimp allergy as described in Leung et al. (*Int. Arch. Allergy Immunol.*, 2008, 147:305-14). Briefly, mice were orally sensitized with 0.1 mg recombinant Met e 1 on days 0, 12, 19, 26 and challenged with 0.5 mg Met e 1 on day 33. The mice were then given three treatments at weekly intervals by intraperitoneal injections of either 0.1 mg KLH alone or a mixture of 0.1 mg mimotope-conjugates from each of cluster 1 to cluster 6 in Alum adjuvant. The mixture of mimotope-conjugagtes included amino acid sequences corresponding to SEQ ID NO: 1 (cluster 1), SEQ ID NO: 3 (cluster 2), SEQ ID NO: 7 (cluster 3), SEQ ID NO: 9 (cluster 4), SEQ ID NO: 13 (cluster 5), and SEQ ID NO: 17 (cluster 6). The mice were challenged again with 0.5 mg Met e 1 one week after the last treatment and the ileum were harvested for RNA extraction. A group of mice receiving 0.1 mg recombinant Met e 1 were included as positive controls. Real-time PCR was performed to detect the expression level of both pro-inflammatory and regulatory cytokine genes. The analysis revealed that there was reduced expression of the pro-inflammatory cytokine genes IL-4 and IL-13 in the intestine after allergen challenge in the mimotope-treated mice compared to the KLH-treated mice, while key regulatory cytokine genes such as IL-10 and TGF-β were up-regulated (FIG. 8). The immunotherapy using a tropomyosin peptide mimotope provided herein induced hyposensitivity in the animal model for shrimp allergy.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

| Informal Sequence Listing | |
|---|---|
| Cluster 1 mimotope<br>RIWVGHFML | SEQ ID NO: 1 |
| Cluster 1 mimotope<br>MRIMHLNWMYWK | SEQ ID NO: 2 |
| Cluster 2 mimotope<br>DIHEESPD | SEQ ID NO: 3 |
| Cluster 2 mimotope<br>HDGIPDWSM | SEQ ID NO: 4 |
| Cluster 3 mimotope<br>PTDVERKTSYTL | SEQ ID NO: 5 |
| Cluster 3 mimotope<br>TKYERGGRVRKI | SEQ ID NO: 6 |
| Cluster 3 mimotope<br>KRLFERDG | SEQ ID NO: 7 |
| Cluster 4 mimotope<br>KGHTKAHHGKNT | SEQ ID NO: 8 |
| Cluster 4 mimotope<br>GTKLQHFRQ | SEQ ID NO: 9 |
| Cluster 4 mimotope<br>VTWERTTKHQHW | SEQ ID NO: 10 |
| Cluster 4 mimotope<br>YKTPHQVFQ | SEQ ID NO: 11 |
| Cluster 5 mimotope<br>RTIPTMHWIH | SEQ ID NO: 12 |
| Cluster 5 mimotope<br>LHTIPVMI | SEQ ID NO: 13 |
| Cluster 5 mimotope<br>IKALSRLQTIYG | SEQ ID NO: 14 |
| Cluster 6 mimotope<br>TFVDDRRFMS | SEQ ID NO: 15 |
| Cluster 6 mimotope<br>HWSSTRRFPP | SEQ ID NO: 16 |
| Cluster 6 mimotope<br>KLAYMHVRV | SEQ ID NO: 17 |
| Cluster 6 mimotope<br>MHVLLMRRD | SEQ ID NO: 18 |
| Cluster 7 mimotope<br>MVGWPPKHRKDK | SEQ ID NO: 19 |
| Cluster 7 mimotope<br>RPWPQAHPNL | SEQ ID NO: 20 |
| Non-clustering mimotope<br>HWHAKNAQR | SEQ ID NO: 21 |
| Non-clustering mimotope<br>WQRHMVHTWRWM | SEQ ID NO: 22 |
| Non-clustering mimotope<br>ASSRWLGKVHDV | SEQ ID NO: 23 |
| Non-clustering mimotope<br>FFEAGKGNK | SEQ ID NO: 24 |
| Non-clustering mimotope<br>RAVFFRNDH | SEQ ID NO: 25 |
| Predicted epitopes<br>MKLEKDNAMDRADTLEQQNKEANNRAEKSEEEVHNLQKRMQQLENDLDQ<br>VQESLLKANNQLVEKDKALSNAEGEVAALNRRIQLLEEDLERSEERLNT<br>ATTKLAEASQAADESERMRKVLENRSLSDEERMDALENQLKEARFLAEE<br>ADRKYDEVARKLAMVEADLERAEERAETGESKIVELEEELRVVGNNLKS<br>LEVSEEKANQREEAYKEQIKTLTNKLKAAEARAEFAERSVQKLQKEVDR<br>LEDELVNEKEKYKSITDELDQTFSELSGY | SEQ ID NO: 26 |
| Met e 1 tropomyosin allergen of *Metapenaeus ensis* (Greasyback shrimp) (*Penaeus ensis*)<br>MKLEKDNAMDRADTLEQQNKEANNRAEKSEEEVHNLQKRMQQLENDLDQ<br>VQESLLKANNQLVEKDKALSNAEGEVAALNRRIQLLEEDLERSEERLNT<br>ATTKLAEASQAADESERMRKVLENRSLSDEERMDALENQLKEARFLAEE<br>ADRKYDEVARKLAMVEADLERAEERAETGESKIVELEEELRVVGNNLKS<br>LEVSEEKANQREEAYKEQIKTLTNKLKAAEARAEFAERSVQKLQKEVDR<br>LEDELVNEKEKYKSITDELDQTFSELSGY | SEQ ID NO: 27 |
| Pen a 1 tropomyosin allergen of *Penaeus monodon* (Giant tiger prawn)<br>MDAIKKKMQAMKLEKDNAMDRADTLEQQNKEANNRAEKSEEEVHNLQKR<br>MQQLENDLDQVQESLLKANIQLVEKDKALSNAEGEVAALNRRIQLLEED<br>LERSEERLNTATTKLAEASQAADESERMRKVLENRSLSDEERMDALENQ<br>LKEARFLAEEADRKYDEVARKLAMVEADLERAEERAETGESKIVELEEE<br>LRVVGNNLKSLEVSEEKANQREEAYKEQIKTLTNKLKAAEARAEFAERS<br>VQKLQKEVDRLEDELVNEKEKYKSITDELDQTFSELSGY | SEQ ID NO: 28 |
| Bet v 1 allergen<br>CQQTLSVRALC | SEQ ID NO: 29 |
| Bet v 1 allergen<br>CGGTPPSLPTC | SEQ ID NO: 30 |
| Bet v 1 allergen<br>CGGTRRPIASC | SEQ ID NO: 31 |

| Informal Sequence Listing | |
|---|---|
| Der p 1 allergen<br>KGIPNTKAP | SEQ ID NO: 32 |
| Der p 1 allergen<br>GIREVWPAG | SEQ ID NO: 33 |
| Der p 1 allergen<br>KGTTGVRNT | SEQ ID NO: 34 |
| Der p 2 allergen<br>FVVEYTKKW | SEQ ID NO: 35 |
| Der p 2 allergen<br>SWWNLPQIG | SEQ ID NO: 36 |
| Der p 2 allergen<br>KGITTKWMA | SEQ ID NO: 37 |
| Der p 2 allergen<br>AGISYTKTW | SEQ ID NO: 38 |
| Bla g 2 allergen<br>SMMKADFDEEPR | SEQ ID NO: 39 |
| Bla g 2 allergen<br>SMMKADFEEEPR | SEQ ID NO: 40 |
| Parvalbumin allergen<br>CYRGVTLAGHRC | SEQ ID NO: 41 |
| Parvalbumin allergen<br>CFKGVRLDGTPC | SEQ ID NO: 42 |
| Parvalbumin allergen<br>CYRGARVDGLMC | SEQ ID NO: 43 |
| Pru p 3 allergen<br>PSRTPRPEWAXL | SEQ ID NO: 44 |
| Pru p 3 allergen<br>TSRPALLNDQGH | SEQ ID NO: 45 |

What is claimed is:

1. An isolated peptide having at least 80% sequence identity to any one of SEQ ID NOS: 3 and 4, wherein the peptide is a mimotope of an epitope of a tropomyosin protein.

2. The peptide of claim 1, wherein the peptide has at least about 85%, 90%, or 95% sequence identity to any one of SEQ ID NOS: 3 and 4.

3. The peptide of claim 1, wherein the peptide comprises at least 8 contiguous amino acids of any one of SEQ ID NOS: 3 and 4.

4. The peptide of claim 1, wherein the peptide comprises an amino acid sequence of any one of SEQ ID NOS: 3 and 4.

5. The peptide of claim 1, wherein the tropomyosin protein is Met e 1 from *Metapenaeus ensis*.

6. The peptide of claim 1, wherein the peptide induces antibodies against the tropomyosin protein.

7. The peptide of claim 1, wherein the peptide is from about 8 to about 25 amino acids in length.

8. The peptide of claim 1, wherein the peptide is from about 8 to about 12 amino acids in length.

9. The peptide of claim 1, wherein the peptide comprises an amino acid sequence consisting of any one of SEQ ID NOS: 3 and 4.

10. The peptide of claim 1, wherein the peptide is conjugated to a carrier protein.

11. A composition comprising a peptide of claim 1 or a plurality thereof and a pharmaceutically acceptable carrier.

12. The composition of claim 11, wherein the plurality of peptides comprises at least 2 different peptides.

13. A kit comprising a peptide of claim 1 or a plurality thereof and instructions for use.

14. The kit of claim 13, wherein the plurality of peptides comprises at least 2 different peptides.

15. A method for inducing antibodies against a tropomyosin protein from shellfish in a subject, the method comprising administering to the subject an effective amount of a peptide of claim 1.

16. A method for preventing, alleviating, or modulating hypersensitivity to shellfish in a subject, the method comprising administering to the subject an effective amount of a peptide of claim 1.

17. A method for developing tolerance or desensitization to a tropomyosin protein from shellfish in a subject, the method comprising administering to the subject an effective amount of a peptide of claim 1.

18. A method for inducing antibodies against a tropomyosin protein from an arthropod in a subject, the method comprising administering to the subject an effective amount of a peptide of claim 1.

19. A method for preventing, alleviating, or modulating hypersensitivity to an arthropod in a subject, the method comprising administering to the subject an effective amount of a peptide of claim 1.

20. A method for developing tolerance or desensitization to a tropomyosin protein from an arthropod in a subject, the method comprising administering to the subject an effective amount of a peptide of claim 1.

* * * * *

UNITED STATES PATENT AND TRADEMARK OFFICE
CERTIFICATE OF CORRECTION

PATENT NO. : 9,920,100 B2
APPLICATION NO. : 15/173467
DATED : March 20, 2018
INVENTOR(S) : Patrick Leung et al.

Page 1 of 1

It is certified that error appears in the above-identified patent and that said Letters Patent is hereby corrected as shown below:

On the Title Page

Please insert item (60):
--(60) Related U.S. Application Data
Provisional application No. 62/171,681, filed on June 5, 2015--.

Signed and Sealed this
Sixteenth Day of October, 2018

Andrei Iancu
*Director of the United States Patent and Trademark Office*